United States Patent
Gomi et al.

(10) Patent No.: US 10,793,818 B2
(45) Date of Patent: Oct. 6, 2020

(54) CULTURE CONTAINER AND CELL CULTURING METHOD AND CELL OBSERVATION METHOD USING CULTURE CONTAINER

(71) Applicants: TOKYO ELECTRON LIMITED, Tokyo (JP); TOCALO CO., LTD., Hyogo (JP)

(72) Inventors: Shinichi Gomi, Tokyo (JP); Kenichi Kagawa, Tokyo (JP); Yusuke Yoda, Tokyo (JP); Shinya Miki, Hyogo (JP); Tatsuya Hamaguchi, Miyagi (JP)

(73) Assignee: TOCALO CO., LTD., Kobe-Shi, Hyogo (JP)

( * ) Notice: Subject to any disclaimer, the term of this patent is extended or adjusted under 35 U.S.C. 154(b) by 416 days.

(21) Appl. No.: 15/753,091

(22) PCT Filed: Aug. 19, 2016

(86) PCT No.: PCT/JP2016/074282
§ 371 (c)(1),
(2) Date: Feb. 15, 2018

(87) PCT Pub. No.: WO2017/030196
PCT Pub. Date: Feb. 23, 2017

(65) Prior Publication Data
US 2018/0201892 A1    Jul. 19, 2018

(30) Foreign Application Priority Data
Aug. 20, 2015 (JP) ................... 2015-163143

(51) Int. Cl.
*C12M 1/22* (2006.01)
*C12M 1/12* (2006.01)
(Continued)

(52) U.S. Cl.
CPC .......... *C12M 25/14* (2013.01); *C12M 1/3453* (2013.01); *C12M 23/00* (2013.01);
(Continued)

(58) Field of Classification Search
CPC ...................................................... C12M 23/10
See application file for complete search history.

(56) References Cited

U.S. PATENT DOCUMENTS 4,741,619 A * 5/1988 Humphries ........... B01L 3/5085
356/246
6,565,813 B1 * 5/2003 Garyantes ........... B01F 13/0071
422/553
(Continued)

FOREIGN PATENT DOCUMENTS

JP    6269979 A    3/1987
JP    5181068 A    7/1993
(Continued)

OTHER PUBLICATIONS

International Search Report dated Sep. 27, 2016 corresponding to application No. PCT/JP2016/074282.

*Primary Examiner* — Jonathan M Hurst
(74) *Attorney, Agent, or Firm* — Nath, Goldberg & Meyer; Jerald L. Meyer

(57) ABSTRACT

The purpose of the present invention is to provide a culture container capable of preventing a concave meniscus without using a jig. In order to achieve this purpose, the present invention provides a culture container (1A) provided with: a base (3) having a concave portion (4); and a water-repellent layer (5) formed on an outer edge region (411) of the bottom (41) of the concave portion (4) and the inner circumferential surface (42) of the concave portion (4). One of the surfaces of the water-repellent layer (5) is exposed to the space in the concave portion (4).

7 Claims, 12 Drawing Sheets

(51) Int. Cl.
*G02B 21/34* (2006.01)
*C12M 1/00* (2006.01)
*C12M 1/34* (2006.01)
*C12N 5/074* (2010.01)
*G02B 21/14* (2006.01)
*C12M 1/32* (2006.01)
*C12Q 1/04* (2006.01)
*G01N 21/03* (2006.01)

(52) U.S. Cl.
CPC ............ *C12M 23/10* (2013.01); *C12M 23/12* (2013.01); *C12M 23/20* (2013.01); *C12M 41/36* (2013.01); *C12N 5/0696* (2013.01); *C12Q 1/045* (2013.01); *G02B 21/14* (2013.01); *G02B 21/34* (2013.01); *C12Q 1/04* (2013.01); *G01N 21/0303* (2013.01); *G01N 2021/0378* (2013.01)

(56) References Cited

U.S. PATENT DOCUMENTS

| | | | |
|---|---|---|---|
| 6,902,705 B1* | 6/2005 | Caillat | C12Q 1/001 422/500 |
| 8,263,391 B2* | 9/2012 | Zantl | B01L 3/5085 356/246 |
| 2005/0244838 A1* | 11/2005 | Wojtowicz | G01N 21/6452 435/287.2 |
| 2007/0274871 A1* | 11/2007 | Jiang | B01L 3/5085 422/400 |
| 2010/0067105 A1* | 3/2010 | Egeler | G01N 21/03 359/398 |

FOREIGN PATENT DOCUMENTS

| | | |
|---|---|---|
| JP | 580299 U | 11/1993 |
| JP | 7216239 A | 8/1995 |
| JP | 2001507218 A | 6/2001 |
| JP | 2001355995 A | 12/2001 |
| JP | 2004245727 A | 9/2004 |

* cited by examiner

CULTURE CONTAINER AND CELL CULTURING METHOD AND CELL OBSERVATION METHOD USING CULTURE CONTAINER

This is a National Phase Application filed under 35 U.S.C. 371 as a national stage of PCT/JP2016/074282, filed Aug. 19, 2016, an application claiming the benefit of Japanese Application No. 2015163143, filed Aug. 20, 2015, the content of each of which is hereby incorporated by reference in its entirety.

TECHNICAL FIELD

The present disclosure relates to a culture container, a method for culturing cells using the culture container, and a method for observing cells using the culture container.

BACKGROUND

As a culture container, there is known a culture container in which an inner surface of a concave portion is subjected to a hydrophilization treatment (see, e.g., Patent Document 1). The hydrophilization treatment of the inner surface of the concave portion is performed for various purposes. For example, when adhering cells are cultured, for the purpose of improving the adhesiveness of cells or a material (e.g., an extracellular matrix) serving as a scaffold of cells to the inner surface of the concave portion, the inner surface of the concave portion is subjected to an oxygen plasma treatment to introduce surface charges. As a result, the inner surface of the concave portion is hydrophilized. In addition, when floating cells are cultured, the inner surface of the concave portion is subjected to a super hydrophilization treatment for the purpose of preventing adhesion of cells or the like to the inner surface of the concave portion due to hydrophobic interaction.

If cell culture is performed using a culture container whose inner surface of a concave portion has been subjected to a hydrophilization treatment, a culture solution in the vicinity of an inner circumferential surface of the concave portion is strongly attracted to the inner circumferential surface of the concave portion. As a result, the thickness of the portion of the culture solution in the vicinity of the inner circumferential surface of the concave portion becomes larger than the thickness of other portions of the culture solution. Thus, a phenomenon in which a liquid surface of the culture solution is bent concavely, namely a concave meniscus, is generated.

The concave meniscus is also generated when the inner circumferential surface of the concave portion is not subjected to a hydrophilization treatment. For example, when components such as amino acids, proteins and the like contained in the culture solution are adsorbed onto the inner circumferential surface of the concave portion and the inner circumferential surface of the concave portion is rendered hydrophilic during cell culture, a concave meniscus is generated.

The concave meniscus causes various problems. For example, when cells are seeded in a culture container, the cell seeding amount per unit area of the bottom surface of the concave portion increases near the inner circumferential surface of the concave portion. Therefore, uniform cell seeding becomes difficult. Moreover, when observing the cells in the culture container with an optical microscope after the cell culture, an optical axis is distorted due to the influence of the inclination of the liquid surface in the vicinity of the inner circumferential surface of the concave portion. Therefore, observation of cells existing in the vicinity of the inner circumferential surface of the concave portion is difficult or impossible.

As a method of preventing the generation of a concave meniscus, there are known a method of inserting a cylindrical body having a water repellent inner surface into a culture container at the time of observation (see Patent Document 2), a method of causing a transparent flat plate to float on a culture liquid (see Patent Document 3), and the like.

On the other hand, as a method of preventing a sample from leaking out from a certain concave portion and entering an adjacent concave portion in a micro-plate having a plurality of concave portions formed therein, there is known a method in which a first region having water repellency is provided from an intermediate portion between an opening and a bottom surface of a concave portion to the opening of the concave portion in the inner surface of the concave portion of the micro-plate and in which a second region having hydrophilicity is provided from the bottom surface of the concave portion to the first region (see Patent Document 4).

PRIOR ART DOCUMENTS

Patent Documents

Patent Document 1: International Application Japanese Translation Publication No. 2001-507218

Patent Document 2: Japanese Laid-open Publication No. 62-69979

Patent Document 3: Japanese Laid-open Publication No. 5-181068

Patent Document 4: Japanese Laid-open Publication No. 2004-245727

However, according to the method of Patent Document 2, the cylindrical body is positioned in the vicinity of the inner circumferential surface of the concave portion. Therefore, it is still difficult or impossible to observe cells in the vicinity of the inner circumferential surface of the concave portion. Furthermore, according to the methods of Patent Document 2 and Patent Document 3, the entry (contamination) of impurities into the culture solution due to the use of a jig (cylindrical body or flat plate) is concerned. In addition, according to the method of Patent Document 4, the region (second region) from the intermediate portion between the opening of the concave portion and the bottom surface to the bottom surface of the concave portion is hydrophilic. Therefore, it is impossible to prevent the generation of the concave meniscus.

The present disclosure provides some embodiments of a culture container, a method for culturing cells using the culture container, and a method for observing cells using the culture container, which are capable of preventing the generation of a concave meniscus without having to use a jig.

SUMMARY

The present disclosure provides the following inventions. (1). A culture container, including: a base having a concave portion; and a water repellent layer formed on an outer edge region of a bottom surface of the concave portion and an inner circumferential surface of the concave portion, wherein one surface of the water repellent layer is exposed to an internal space of the concave portion.

(2). The culture container of (1), wherein the bottom surface of the concave portion is a flat surface.

(3). The culture container of (1) or (2), wherein a contact angle between one surface of the water repellent layer and water is 115 degrees or more.

(4). The culture container of any one of (1) to (3), further including: a DLC layer formed on the side of the other surface of the water repellent layer.

(5). The culture container of (4), further including: an adhesion layer formed between the water repellent layer and the DLC layer.

(6). A method of culturing cells using the culture container of any one of (1) to (5), including: forming an extracellular matrix layer in a region other than the outer edge region in the bottom surface of the concave portion before seeding the cells in the concave portion.

(7). A method of observing cells using the culture container of any one of (1) to (5), including: observing the cells in the concave portion with a phase difference microscope from the side of the bottom surface of the concave portion or the side of an opening of the concave portion.

According to the present disclosure, it is possible to provide a culture container, a method for culturing cells using the culture container, and a method for observing cells using the culture container, which are capable of preventing the generation of a concave meniscus without having to use a jig.

DETAILED DESCRIPTION

Embodiments of the present disclosure will now be described with reference to the drawings.

First Embodiment

A culture container 10A according to a first embodiment is a culture container for microscope observation, namely a culture container capable of culturing cells and capable of microscope observation of cultured cells. Therefore, the culture container 10A is configured to satisfy the conditions required for the container for cell culture and the conditions required for the container for microscope observation. However, the configuration of the culture container 10A may be appropriately changed as long as the cell culture is possible. When the culture container is not for microscope observation, it is not necessary to satisfy the conditions required for the container for microscope observation.

Examples of the cells cultured in the culture container 10A include floating cells, adhering cells, and the like. Examples of the adhering cells include pluripotent stem cells (e.g., embryonic stem cells (ES cells), induced pluripotent stem cells (iPS cells), etc.), stem cells, progenitor cells, somatic cells, reproductive cells, and the like. Examples of the floating cells include hemocyte cells such as T cells and B cells, and the like. The cells cultured in the culture container 10A may form a tissue. Examples of the tissue include a cartilage tissue, a bone tissue, a muscle tissue, a corneal tissue, a vascular tissue, and the like. The tissue may be a tissue separated from a living body or a tissue differentiated from a stem cell.

Figure 1:
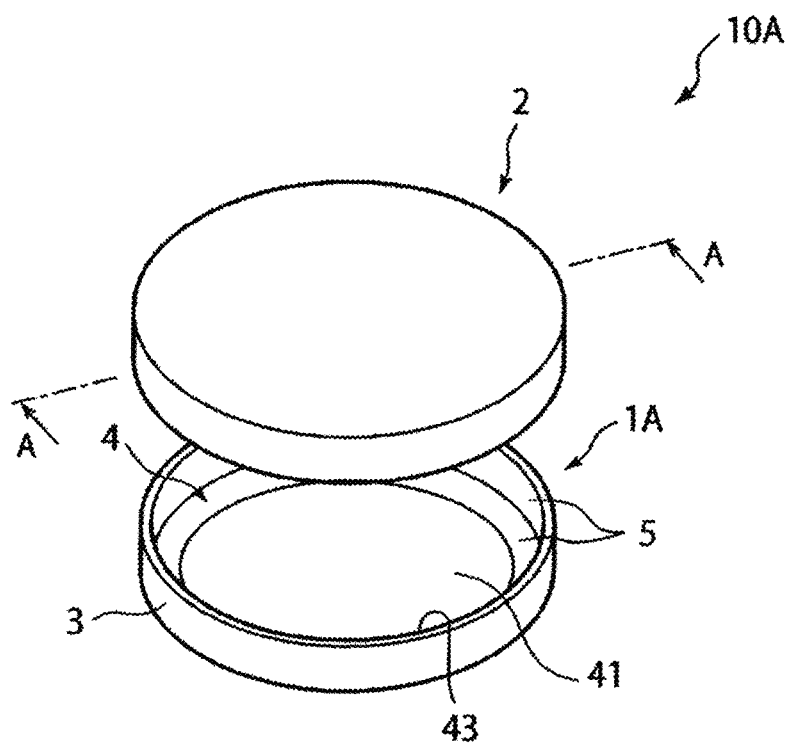
FIG. 1 is a perspective view of a culture container according to a first embodiment.
Figure 2:
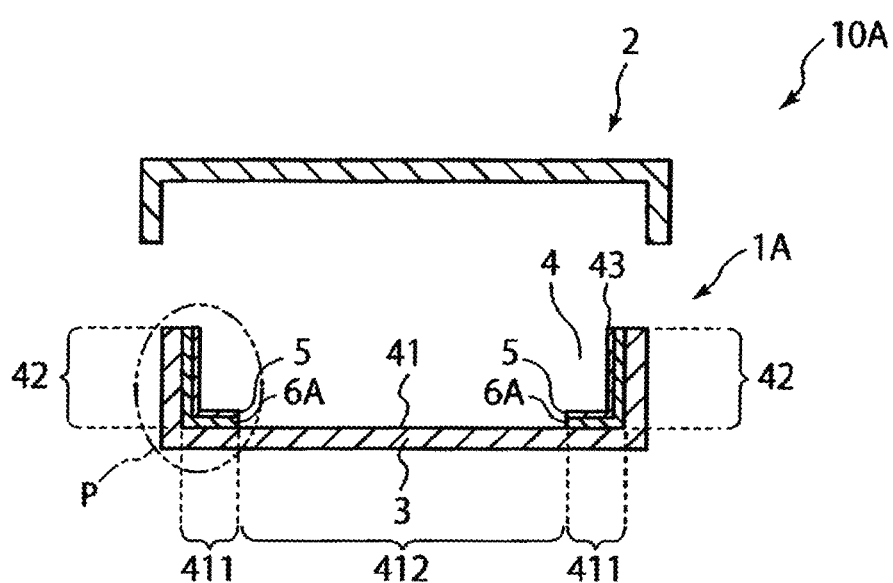
FIG. 2 is a sectional view of the culture container taken along line A-A in FIG. 1.

As shown in FIG. 1 and FIG. 2, the culture container 10A includes a culture container body 1A and a lid 2.

As shown in FIGS. 1 and 2, the culture container body 1A includes a base 3 having a concave portion 4, and a water repellent layer 5 formed in an outer edge region 411 of a bottom surface 41 of the concave portion 4 and on an inner circumferential surface 42 of the concave portion 4. Of two surfaces of an arbitrary layer including the water repellent layer 5, the surface at the space side in the concave portion 4 is referred to as "one surface", and the surface at the opposite side is referred to as "the other surface" in some cases.

In the present embodiment, the base 3 is a dish which is φ100 mm in diameter, φ60 mm in diameter, φ35 mm in diameter, or like. The number of concave portions of the base 3 is one. However, the number of the concave portions of the base 3 may be appropriately changed depending on the use of the culture container. The number of the concave portions of the base 3 may be two or more. In the case where the number of the concave portions of the base 3 is two or more, each concave portion may be configured in the same manner as the concave portion 4. Examples of the base having two or more concave portions include a multi-well plate having cylindrical wells of 6 holes, 24 holes, 48 holes or 96 holes, and the like.

Figure 4:
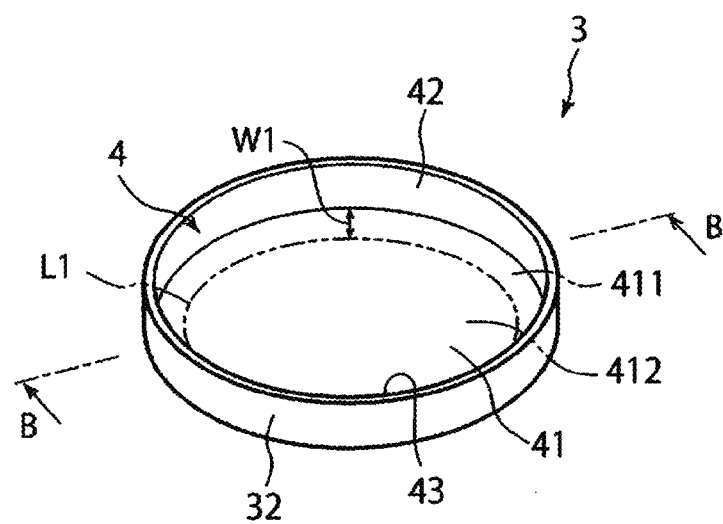
FIG. 4 is a perspective view of a base included in a culture container body of the culture container shown in FIG. 1.
Figure 5:
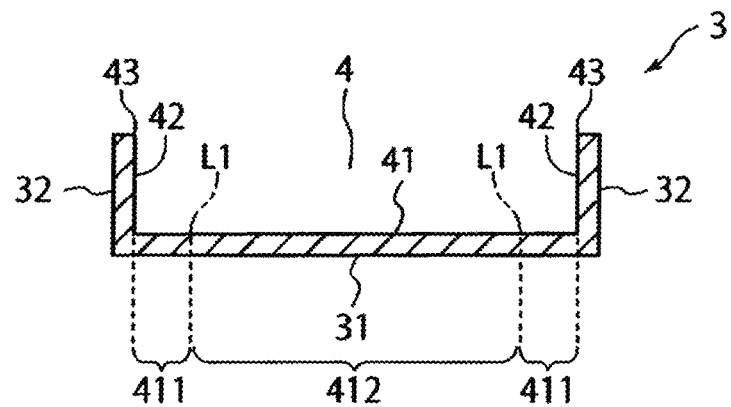
FIG. 5 is a sectional view of the base taken along line B-B in FIG. 4.

As shown in FIGS. 4 and 5, the base 3 includes a bottom wall portion 31 and a side wall portion 32 which stands up from the peripheral edge of the bottom wall portion 31 to form the concave portion 4. In the present embodiment, the bottom wall portion 31 and the side wall portion 32 are integrally formed. The bottom wall portion 31 is formed of a flat plate member having a substantially uniform thickness. The inner wall surface of the bottom wall portion 31 and the outer wall surface at the opposite side thereof are flat. The side wall portion 32 is formed of a cylindrical member having a substantially uniform thickness. The inner wall surface of the side wall portion 32 and the outer wall surface at the opposite side thereof are post surfaces (developable surfaces). However, the shapes of the bottom wall portion 31 and the side wall portion 32 may be appropriately changed depending on the use of the culture container.

The fact that the inner wall surface of the bottom wall portion 31 is flat is a condition adapted for the case where the cells cultured in the culture container 10A are adhering cells. The reason for this is the same as the reason (described later) that the bottom surface 41 of the concave portion 4 is preferably flat.

The fact that the inner wall surface of the bottom wall portion 31 and the outer wall surface at the opposite side thereof are flat is a condition adapted for the case where the cells cultured in the concave portion 4 are observed with a microscope. That is to say, if this condition is satisfied, it is possible to enhance the accuracy of microscope observation utilizing the light transmissivity of the bottom wall portion 31. Examples of the microscope observation utilizing the light transmissivity of the bottom wall portion 31 include a transmission-type upright microscope observation in which light is irradiated from below the culture container body 1A and the transmitted light is received above the culture container body 1A, a transmission-type inverted microscope observation in which light is irradiated from above the culture container body 1A and the transmitted light is received below the culture container body 1A, and an incident-light-type inverted microscope observation in which light is irradiated from below the culture container body 1A and the reflected light is received below the culture container body 1A.

The entire inner wall surface of the bottom wall portion 31 and the entire inner wall surface of the side wall portion 32 are subjected to a hydrophilization treatment. Examples of the hydrophilization treatment include introduction of a hydrophilic functional group to the inner wall surfaces, formation of a hydrophilic layer on the inner wall surfaces, and the like. The hydrophilization treatment may be carried out according to a hydrophilization treatment commonly performed with respect to a culture container. For example, a hydrophilic functional group may be introduced to the inner wall surfaces by a treatment such as a plasma treatment, a corona discharge treatment, ultraviolet irradiation or the like. Furthermore, a hydrophilic layer may be formed on the inner wall surfaces by coating a raw material solution for the hydrophilic layer (e.g., a solution of a hydrophilic substance such as collagen, gelatin, fibronectin, laminin, polylysine, thrombospondin, vitronectin, or the like) on the inner wall surfaces by, for example, spraying, dipping, brush coating or the like and then curing the raw material solution. The curing treatment may be carried out using a heating method, a room temperature leaving method, a plasma method, or the like. When forming the hydrophilic layer, the hydrophilic layer may be bonded to the inner wall surfaces by a chemical reaction, a plasma reaction, or a reaction using electronic beams, radioactive rays or ultraviolet rays.

In the present embodiment, the material constituting the bottom wall portion 31 is a light transmissive material. Examples of the light transmissive material include plastics, glass, ceramics and the like. Examples of the plastics include polystyrene, polyethylene, polypropylene, polycarbonate, polyester (e.g., polyethylene terephthalate), acrylic resin (e.g., polymethyl methacrylate), and the like. Examples of the glass include silica glass and the like. Examples of the ceramics include silica and the like.

The fact that the material constituting the bottom wall portion 31 is a light transmissive material is a condition adapted for the case where the cells cultured in the concave portion 4 are observed with a microscope. That is to say, if this condition is satisfied, it is possible to enhance the accuracy of the microscope observation utilizing the light transmissivity of the bottom wall portion 31.

The material constituting the side wall portion 32 may be a light transmissive material or a light non-transmissive material. In the present embodiment, the bottom wall portion 31 and the side wall portion 32 are integrally molded. Therefore, the side wall portion 32 is made of a light transmissive material just like the bottom wall portion 31. Examples of the light non-transmissive material include ceramics such as alumina or the like, plastics colored with white, black or the like, and so forth.

As shown in FIGS. 4 and 5, the concave portion 4 includes a bottom surface 41, an inner circumferential surface 42 standing up from the peripheral edge of the bottom surface 41, and an opening 43 located at the opposite side of the bottom surface 41.

As shown in FIGS. 4 and 5, the bottom surface 41 of the concave portion 4 is partitioned by a boundary line L1 into an outer edge region 411 and a central region 412 located inward of the outer edge region 411. The boundary line L1 is a virtual line. The outer edge region 411 and the central region 412 are virtual regions.

The boundary line L1 is a ring-shaped line positioned inward of an outer peripheral line of the bottom surface 41. In the present embodiment, the boundary line L1 has a circular shape but may have other ring shapes. Examples of the other ring shapes include an elliptical shape, a rectangular shape and the like.

The outer edge region 411 is an annular region extending along the outer peripheral line of the bottom surface 41. The outer peripheral line of the outer edge region 411 coincides with the outer peripheral line of the bottom surface 41. The inner peripheral line of the outer edge region 411 coincides with the boundary line L1. The outer edge region 411 has a width W1. The width W1 is the distance between the outer peripheral line of the bottom surface 41 and the boundary line L1.

The outer edge region 411 is a region where cells are difficult to adhere, because the water repellent layer 5 is formed in the outer edge region 411. Therefore, when the cells cultured in the culture container 10A are adhering cells, the width W1 of the outer edge region 411 may be small. In the case where the cells cultured in the culture container 10A are adhering cells, the width W1 of the outer edge region 411 may be adjusted so that the ratio of the area of the outer edge region 411 to the area of the bottom surface 41 becomes 85% or less, specifically 50% or less. The lower limit of the ratio of the area of the outer edge region 411 to the area of the bottom surface 41 is not particularly limited, but may be 5%, specifically 10%. For example, when the radius of the bottom surface 41 is 17.5 mm or more, the width W1 of the outer edge region 411 may be adjusted to be 10 mm or less, specifically 5 mm or less. The lower limit value of the width W1 of the outer edge region 411 is not particularly limited, but may be 0.5 mm, specifically 1 mm.

The bottom surface 41 of the concave portion 4 is formed by the inner wall surface of the bottom wall portion 31 of the base 3 or one surface of the hydrophilic layer formed on the inner wall surface of the bottom wall portion 31. The inner circumferential surface 42 of the concave portion 4 is formed by the inner wall surface of the side wall portion 32 of the base 3 or one surface of the hydrophilic layer formed on the inner wall surface of the side wall portion 32 of the base 3.

The bottom surface 41 of the concave portion 4 is a flat surface, and the inner circumferential surface 42 of the concave portion 4 is a cylindrical surface (a developable surface). The plan-view shape of the concave portion 4 is a circular shape. The sectional-view shape of the concave portion 4 is a rectangular shape. However, the plan-view shape and the sectional-view shape of the concave portion 4 may be appropriately changed. The plan-view shape of the concave portion 4 may be, for example, an elliptical shape, a rectangular shape or the like. The sectional-view shape of the concave portion 4 may be, for example, a trapezoidal shape or the like. In the case where the sectional-view shape of the concave portion 4 is a trapezoidal shape, the shorter one of the upper side and the lower side of the trapezoid may be positioned at the side of the bottom surface 41 of the concave portion 4 so that the entire bottom surface 41 can be visually recognized from the opening 43.

Figure 6:
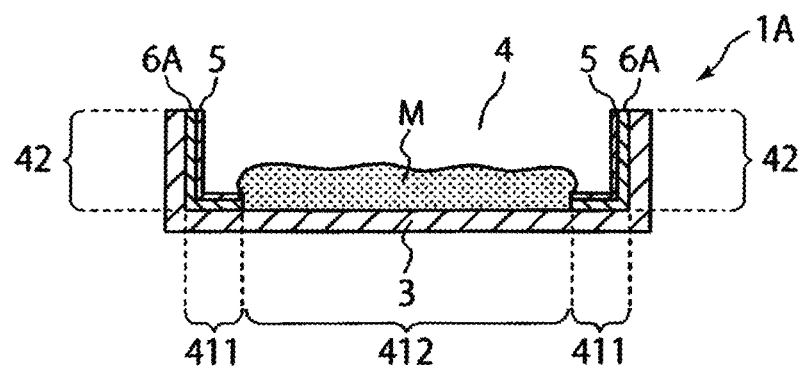
FIG. 6 is a view for explaining a step of forming an extracellular matrix layer.

The fact that the bottom surface 41 of the concave portion 4 is a flat surface is a condition adapted for the case where the cells cultured in the culture container 10A are adhering cells. That is to say, if this condition is satisfied, it is advantageous when an extracellular matrix layer serving as a scaffold of adhering cells is formed in the central region 412 of the bottom surface 41 of the concave portion 4. Specifically, as shown in FIG. 6, when forming an extracellular matrix layer, if an extracellular matrix solution M added to the central region 412 of the bottom surface 41 of the concave portion 4 and spreading toward the peripheral edge of the bottom surface 41 reaches the outer edge region 411 of the bottom surface 41, the extracellular matrix solution M is repelled by the water repellent layer 5 formed in the outer edge region 411. Thus, the extracellular matrix solution M forms a droplet shape and remains in the central region 412. Therefore, it is possible to cause the extracellular matrix to be efficiently adsorbed to a portion or the entirety of the central region 412. This provides the following two major effects. One effect is that the extracellular matrix solution M can be selectively introduced into only the central region 412 in which cell culture is performed, thereby reducing the loss of the extracellular matrix which is generally expensive. The other effect is that the adsorption of the extracellular matrix to the water repellent layer 5 formed on the inner circumferential surface 42 of the concave portion 4 is suppressed, thereby making it possible to prevent the generation of a concave meniscus due to the adsorption of the extracellular matrix onto the water repellent layer 5 formed on the inner circumferential surface 42 of the concave portion 4 and the hydrophilization of the surface of the water repellent layer 5. Usually, the concentration of the proteins contained in the extracellular matrix solution M is very high, and the adsorbability of the proteins is quite high as compared with general proteins. If the water repellent layer 5 is not formed in the outer edge region 411 of the bottom surface 41 and if the water repellent layer 5 is formed only on the inner circumferential surface 42, the extracellular matrix solution M easily reaches the inner circumferential surface 42 of the concave portion 4, thereby lowering the water repellency thereof. Thus, the effect of suppressing the generation of the concave meniscus is impaired. Accordingly, by forming the water repellent layer 5 not only on the inner circumferential surface 42 of the concave portion 4 but also in a region (i.e., the outer edge region 411) partially expanding further inward of the side of the bottom surface 41 from the inner circumferential surface 42, even if the extracellular matrix is adsorbed onto the water repellent layer 5 formed in the outer edge region 411 of the bottom surface 41 and the water repellency of the water repellent layer 5 is impaired, it is possible to prevent the surface of the water repellent layer 5 from becoming hydrophilic due to the adsorption of the extracellular matrix onto the water repellent layer 5 formed on the inner circumferential surface 42 of the concave portion 4. Therefore, it is possible to prevent components in the culture solution from being attracted to the water repellent layer 5 formed on the inner circumferential surface 42 of the concave portion 4. This makes it possible to prevent the generation of a concave meniscus.

Since the entire inner wall surface of the bottom wall portion 31 and the entire inner wall surface of the side wall portion 32 are subjected to the hydrophilization treatment, the bottom surface 41 and the inner circumferential surface 42 of the concave portion 4 have hydrophilicity. The fact that at least the central region 412 of the bottom surface 41 of the concave portion 4 has hydrophilicity is a condition adapted for the case where the cells cultured in the culture container 10A are adhering cells. That is to say, if this condition is satisfied, it is advantageous when an extracellular matrix layer serving as a scaffold of adhering cells is formed in the central region 412 of the bottom surface 41 of the concave portion 4. Specifically, when forming the extracellular matrix layer, components in the extracellular matrix solution added to the central region 412 of the bottom surface 41 of the concave portion 4 are more likely to be adsorbed onto the central region 412 of the bottom surface 41.

As shown in FIGS. 1 and 2, the water repellent layer 5 is formed on the outer edge region 411 of the bottom surface 41 of the concave portion 4 and the inner circumferential surface 42 of the concave portion 4. In the present disclosure, the phrase "the water repellent layer is formed on the outer edge region of the bottom surface of the concave portion and the inner circumferential surface of the concave portion" means that the water repellent layer is formed on the entire outer edge region of the bottom surface of the concave portion and the entire inner circumferential surface of the concave portion either directly or via an intermediate layer composed of one or more layers. In the present embodiment, as shown in FIGS. 1 and 2, the water repellent layer 5 is formed on the entire outer edge region 411 of the bottom surface 41 of the concave portion 4 and the entire inner circumferential surface 42 of the concave portion 4 via an intermediate layer 6A.

As shown in FIGS. 1 and 2, one surface of the water repellent layer 5 is exposed to an internal space of the concave portion 4, and the other surface of the water repellent layer 5 is in contact with one surface of the intermediate layer 6A. One surface of the intermediate layer 6A is in contact with the other surface of the water repellent layer 5, and the other surface of the intermediate layer 6A is in contact with the outer edge region 411 of the bottom surface 41 of the concave portion 4 and the inner circumferential surface 42 of the concave portion 4.

As shown in FIGS. 1 and 2, the intermediate layer 6A is formed on the entire outer edge region 411 of the bottom surface 41 of the concave portion 4 and the entire inner circumferential surface 42 of the concave portion 4. The intermediate layer 6A includes a first portion extending over the entire outer edge region 411 of the bottom surface 41 and a second portion extending over the entire inner circumferential surface 42. An edge portion of the first portion of the intermediate layer 6A at the side of the inner circumferential surface 42 is continuous with an edge portion of the second portion of the intermediate layer 6A at the side of the bottom surface 41. An edge portion at the side of the boundary line L1 in the first portion of the intermediate layer 6A coincides with the boundary line L1 in a plan view.

As shown in FIGS. 1 and 2, the water repellent layer 5 is formed on one entire surface of the intermediate layer 6A. One surface of the intermediate layer 6A includes a first region corresponding to the surface of the first portion of the intermediate layer 6A and a second region corresponding to the surface of the second portion of the intermediate layer 6A. The water repellent layer 5 includes a first portion extending over the entire first region of one surface of the intermediate layer 6A and a second portion extending over the entire second region of one surface of the intermediate layer 6A. An edge portion at the side of the inner circumferential surface 42 in the first portion of the water repellent layer 5 is continuous with an edge portion at the side of the bottom surface 41 in the second portion of the water repellent layer 5. An edge portion at the side of the boundary line L1 in the first portion of the water repellent layer 5 coincides with the boundary line L1 in a plan view.

The water repellent layer 5 contains a water repelling agent. Examples of the water repelling agent include polysiloxane, polysiloxane into which an organic group and/or a fluorine atom is introduced, fluororesin and the like. Examples of the organic group to be introduced into polysiloxane include an alkyl group such as a methyl group, an ethyl group, a propyl group or the like, an aryl group such as a vinyl group, a phenyl group or the like, and so forth. Examples of the fluororesin include polytetrafluoroethylene (PTFE), tetrafluoroethylene-perfluoroalkylvinylether copolymer (PFA), tetrafluoroethylene-hexafluoropropylene copolymer (FEP), tetrafluoroethylene-ethylene copolymer (ETFE), polyvinylidene fluoride (PVDF), polychlorotrifluoroethylene (PCTFE,), and the like. In addition to the water repelling agent, the water repellent layer 5 may contain a primer component. The primer component has a functional group capable of bonding with a functional group of a substance constituting a layer (in the present embodiment, an adhesion layer 62A) adjacent to the water repellent layer 5. Examples of the primer component include a silane coupling agent and the like. For example, a silanol group of a silane coupling agent bonds with a hydroxyl group of a substance constituting the adhesion layer 62A to form a siloxane bond, whereby the bonding force between the water repellent layer 5 and the adhesion layer 62A can be enhanced.

The thickness of the water repellent layer 5 may be 0.01 to 0.2 μm. The water repellent layer 5 may be formed by coating a raw material solution for the water repellent layer (e.g., a water repelling agent solution) on the surface, on which the water repellent layer 5 is to be formed, by using a method such as spraying, dipping, brush coating or the like, and subsequently curing the raw material solution. The curing treatment may be performed using a heating method, a room temperature leaving method, a plasma method or the like. When forming the water repellent layer 5, the water repellent layer 5 may be bonded to the surface, on which the water repellent layer 5 is to be formed, by a chemical reaction, a plasma reaction, or a reaction using electronic beams, radiative rays or ultraviolet rays.

Among the two surfaces of the water repellent layer 5, one surface exposed to the internal space of the concave portion 4 has water repellency. In the present disclosure, the term "water repellency" means that the contact angle between one surface of the water repellent layer and water is 90 degrees or more. The contact angle between one surface of the water repellent layer 5 and water may be 105 degrees or more, specifically 115 degrees or more. The contact angle referred to here is a contact angle when pure water is used. A θ/2 method is employed as a contact angle measurement method. For measurement of the contact angle, a commercially available contact angle measuring device (e.g., PG-X manufactured by Matsubo Corporation, etc.) can be used.

Figure 3:
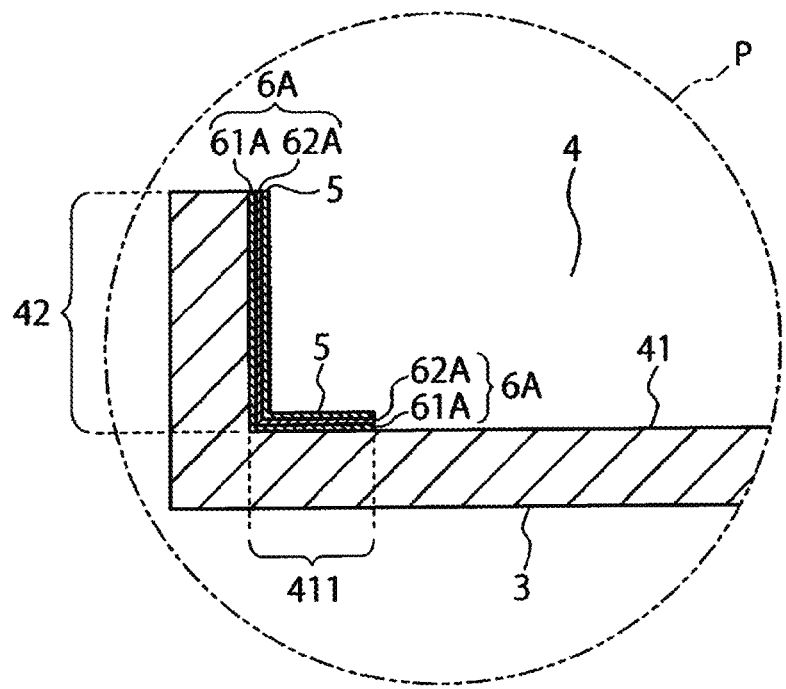
FIG. 3 is an enlarged view of a portion denoted by reference symbol P in FIG. 2.

As shown in FIG. 3, the intermediate layer 6A includes a DLC layer 61A formed at the side of the other surface of the water repellent layer 5 and an adhesion layer 62A formed between the water repellent layer 5 and the DLC layer 61A. In the present disclosure, the term "DLC" refers to diamond-like carbon.

The DLC layer 61A is formed on the entire outer edge region 411 of the bottom surface 41 of the concave portion 4 and the entire inner circumferential surface 42 of the concave portion 4. The adhesion layer 62A is formed on the entire one surface of the DLC layer 61A. The water repellent layer 5 is formed on the entire one surface of the adhesion layer 62A.

The DLC layer 61A can improve the water repellency of the water repellent layer 5. The DLC layer 61A also serves as a barrier layer for preventing components of the adhesion layer 62A from dissolving the base 3.

A thickness of the DLC layer 61A may be 0.1 to 1.0 μm. The DLC layer is a hard film containing hydrocarbon as a main component and is a mixture of a diamond structure (SP3 structure) and a graphite structure (SP2 structure) while being amorphous. A portion of the hydrogen atoms contained in the DLC layer may be substituted with fluorine atoms. Examples of a method for forming the DLC layer include an ionization vapor deposition method, an arc ion plating method, a high frequency/high voltage pulse superimposition type deposition method, a plasma booster method, a plasma CVD method, and the like. Examples of the raw material gas used for forming the DLC layer include a hydrocarbon gas and the like. Examples of hydrocarbon include $CH_3$, $CH_2CH_2$, $C_2H_2$, $CH_3CH_2CH_3$, $CH_3CH_2CH_2CH_3$, $C_6H_5CH_3$, $C_6H_5CH_2CH$, $C_6H_4(CH_3)_2$, $CH_3(CH_2)_4CH_3$ and the like.

The adhesion layer 62A allows the water repellent layer 5 and the DLC layer 61 to more strongly adhere to each other.

A thickness of the adhesion layer 62A may be 0.1 to 1.5 μm. Examples of the adhesion layer 62A include a silica layer, a zirconia layer, a titania layer and the like. The adhesion layer 62A may be formed by coating a raw material solution for the adhesion layer 62A (e.g., an ethyl silicate (TEOS) solution in the case of a silica layer, a normal butyl zirconate (NBZ) solution in the case of a zirconia layer, and a butyl titanate dimer (DBT) solution in the case of a titania layer) on the surface, on which the adhesion layer 62A is to be formed, by using a method such as spraying, dipping, brush coating or the like, and subsequently curing the raw material solution. The curing treatment can be performed using a heating method, a room temperature leaving method, a plasma method or the like. When forming the adhesion layer 62A, the adhesion layer 62A may be bonded to the surface, on which the adhesion layer 62A is to be formed, by a chemical reaction, a plasma reaction, or a reaction using electronic beams, radiative rays or ultraviolet rays.

As the water repellent layer 5 is formed on the entire outer edge region 411 of the bottom surface 41 of the concave portion 4 and the entire inner circumferential surface 42 of the concave portion 4 via the intermediate layer 6A, a culture chamber is formed inside the concave portion 4. One surface of the water repellent layer 5 is exposed to the internal space of the concave portion 4. In one surface of the water repellent layer 5, a region corresponding to the surface of the first portion of the water repellent layer 5 forms an outer edge region of a bottom surface of the culture chamber, a region corresponding to the surface of the second portion of the water repellent layer 5 forms an inner circumferential surface of the culture chamber. As a result, water repellency is imparted to the outer edge region of the bottom surface of the culture chamber and the inner circumferential surface of the culture chamber. In the bottom surface 41 of the concave portion 4, a region where the water repellent layer 5 is not formed, namely the central region 412, is exposed to the internal space of the concave portion 4, thereby forming the central region of the bottom surface of the culture chamber. As a result, hydrophilicity is imparted to the central region of the bottom surface of the culture chamber.

The lid 2 is configured to be detachable from the culture container body 1A. When the lid 2 is attached to the culture container body 1A, the opening 43 of the concave portion 4 is sealed. This makes it possible to prevent (entry) contamination of impurities into the concave portion 4.

A portion of the lid 2, which seals the opening 43 of the concave portion 4, is formed of a flat plate member having a substantially uniform thickness. An inner wall surface of the portion (a wall surface at the side of the opening 43) and an outer wall surface opposite to the inner wall surface are flat surfaces. The configuration of the lid 2 may be appropriately changed depending on the use of the culture container.

The fact that the inner wall surface of the portion of the lid 2 that seals the opening 43 of the concave portion 4 and the outer wall surface opposite to the inner wall surface are flat surfaces is a condition adapted for the case where the cells cultured in the concave portion 4 are observed with a microscope. That is to say, if this condition is satisfied, it is possible to enhance the accuracy of microscope observation utilizing the light transmissivity of the lid 2. Examples of the microscope observation utilizing the light transmissivity of the lid 2 include a transmission-type upright microscope observation in which light is irradiated from below the culture container body 1A and the transmitted light is received above the culture container body 1A, a reflection-type upright microscope observation in which light is irradiated from above the culture container body 1A and the reflected light is received above the culture container body 1A, and a transmission-type inverted microscope observation in which light is irradiated from above the culture container body 1A and the transmitted light is received below the culture container body 1A.

In the present embodiment, the material constituting the lid 2 is a light transmissive material. Specific examples similar to those of the culture container body 1A may be cited as the light transmissive material. When the lid 2 is not attached to the culture container body 1A in the microscope observation, the material constituting the lid 2 may be a light non-transmissive material.

The fact that the material constituting the lid 2 is a light transmissive material is a condition adapted for the case where the cells cultured in the concave portion 4 are observed with a microscope. That is to say, if this condition is satisfied, it is possible to enhance the accuracy of the microscope observation utilizing the light transmissivity of the lid 2.

The culture container body 1A may be manufactured by a method including:

(A1) a step of preparing the base 3 having the concave portion 4 formed therein;

(A2) a step of masking the central region 412 of the bottom surface 41 of the concave portion 4;

(A3) a step of forming the DLC layer 61A on the entire outer edge region 411 of the bottom surface 41 of the concave portion 4 and the entire inner circumferential surface 42 of the concave portion 4;

(A4) a step of forming the adhesion layer 62A on the entire one surface of the DLC layer 61A formed in step (A3); and (A5) forming the water repellent layer 5 on the entire one surface of the adhesion layer 62A formed in step (A4).

In step (A1), for example, a commercially available base is prepared as the base 3 having the concave portion 4. The base is usually sold as a set with a lid. For example, a base in which a hydrophilization treatment is applied to the entire inner wall surface of the bottom wall portion and the entire inner wall surface of the side wall portion, a base in which a hydrophilization treatment is not applied to the entire inner wall surface of the bottom wall portion and the entire inner wall surface of the side wall portion (e.g., a base in which polystyrene constituting the bottom wall portion and the side wall portion is exposed to the inner wall surface of the bottom wall portion and the inner wall surface of the side wall portion), and the like are commercially available. When the cells cultured in the culture container 10A are adhering cells, a base in which at least the central region of the bottom surface of the concave portion is subjected to a hydrophilization treatment may be used. The use of such a base is advantageous when an extracellular matrix layer serving as a scaffold for adhering cells is formed in the central region of the bottom surface of the concave portion. Therefore, a base in which the entire inner wall surface of the bottom wall portion and the entire inner wall surface of the side wall portion are subjected to a hydrophilization treatment may be used as the base 3. In the case of using a base in which the entire inner wall surface of the bottom wall portion and the entire inner wall surface of the side wall portion are not subjected to a hydrophilization treatment, the base may be used as the base 3 after at least the central region of the bottom surface of the concave portion is subjected to a hydrophilization treatment. The description on the hydrophilization treatment is the same as above and therefore will be omitted.

In step (A2), for example, a commercially available masking material is used to cover the central region 412 of the bottom surface 41 of the concave portion 4. The material and shape of the masking material is not particularly limited as long as the masking material can protect the central region 412 from various processes (a DLC layer forming process, an adhesion layer forming process, a water repellent layer forming process, etc.) used in subsequent steps. In step (A2), by covering the central region 412 with a masking material having an arbitrary diameter smaller than the diameter of the bottom surface 41 of the concave portion 4, it is possible to form the outer edge region 411 with an arbitrary width on the bottom surface 41 of the concave portion 4.

In step (A3), the DLC layer 61A is formed on the entire outer edge region 411 of the bottom surface 41 of the concave portion 4 and the entire inner circumferential surface 42 of the concave portion 4 using, for example, a plasma CVD method. In the plasma CVD method, a raw material gas of the DLC layer 61A is converted into plasma to form the DLC layer 61A on the entire outer edge region 411 of the bottom surface 41 of the concave portion 4 and the entire inner circumferential surface 42 of the concave portion 4.

In step (A4), the adhesion layer 62A is formed on the entire one surface of the DLC layer 61A by coating a raw material solution for the adhesion layer 62A on the entire one surface of the DLC layer 61A by, for example, a method such as spraying, dipping, brush coating or the like, and subsequently curing the raw material solution.

In step (A5), the water repellent layer 5 is formed on the entire one surface of the adhesion layer 62A by coating a raw material solution for the water repellent layer 5 on the entire one surface of the adhesion layer 62A by, for example, a method such as spraying, dipping, brush coating or the like, and subsequently curing the raw material solution.

Hereinafter, a cell culturing method using the culture container 10A will be described. In the present embodiment, the culture container body 1A is used in combination with the lid 2. However, the culture container body 1A may be used alone.

The culture container body 1A and the lid 2 may be sterilized before being used for cell culture. Examples of the sterilization method include a method of heat-treating in an autoclave, a method of sterilizing with an ethylene oxide gas, a method of irradiating radiative rays such as gamma rays, electronic beams, ultraviolet rays or the like, and so forth. It has been confirmed that the water repellent layer 5 composed of a compound containing a fluorinated polysiloxane maintains a surface function (i.e., water repellency) even after it is subjected to an autoclave, ethylene oxide or gamma ray sterilization treatment.

Figure 7A:
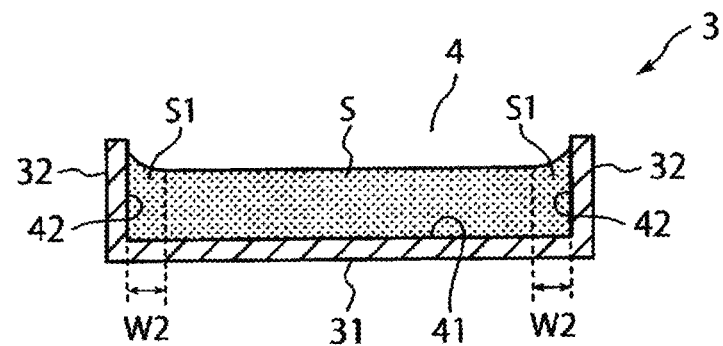
FIG. 7A is a view for explaining a concave meniscus generated when a water repellent layer is not formed.
Figure 7B:
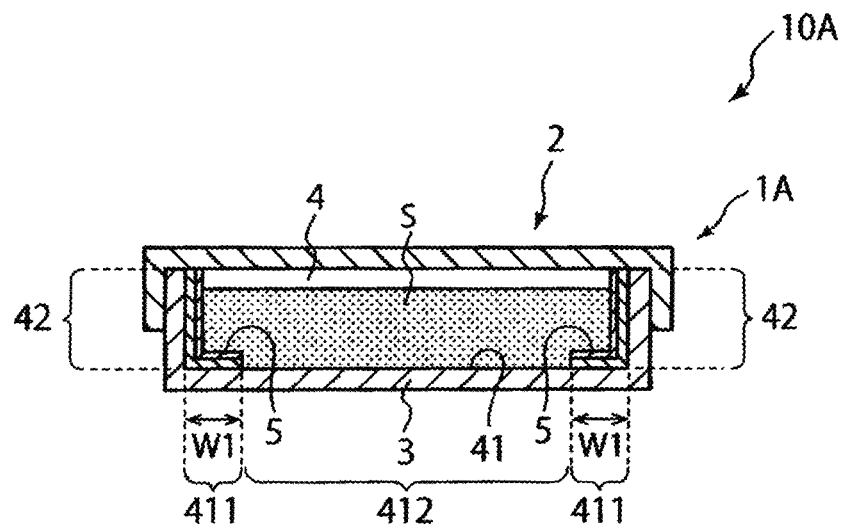
FIG. 7B is a view for explaining that the generation of a concave meniscus is prevented by forming a water repellent layer in the culture container shown in FIG. 1.

In the cell culture method using the culture container 10A, first, culture materials such as cells, a culture solution and the like are accommodated in the concave portion 4 of the culture container body 1A (cell seeding step). In the case of a conventional typical culture container, the water repellent layer 5 is not formed on the inner circumferential surface 42 of the concave portion 4, and the inner circumferential surface 42 of the concave portion 4 having hydrophilicity is exposed to the internal space of the concave portion 4. Therefore, as shown in FIGS. 7A and 7B, when a culture solution S is stored inside the concave portion 4, the culture solution S is strongly attracted to the inner circumferential surface 42. As a result, the thickness of the portion S1 of the culture solution S in the vicinity of the inner circumferential surface 42 becomes larger than the thickness of other portions of the culture solution S. Thus, there is generated a phenomenon that the liquid surface of the culture solution S is bent concavely, namely a concave meniscus. The portion S1 of the culture solution S in the vicinity of the inner circumferential surface 42 has a width W2. The width W2 is the distance between the inflection point of the liquid surface of the culture solution S and the inner circumferential surface 42 of the concave portion 4. In the conventional typical culture container, the thickness of the portion S1 of the culture solution S in the vicinity of the inner circumferential surface 42 is larger than the thickness of the central portion of the culture solution S due to the influence of the concave meniscus. Therefore, a cell seeding amount per a unit area of the bottom surface 41 of the concave portion 4 increases in the vicinity of the inner circumferential surface 42 of the concave portion 4, whereby the cell seeding becomes non-uniform. In contrast, in the culture container body 1A according to the present embodiment, the water repellent layer 5 is formed on the bottom surface 41 and the inner circumferential surface 42 of the concave portion 4. Therefore, the culture solution existing in the vicinity of the inner circumferential surface 42 of the concave portion 4 is not strongly attracted to the inner circumferential surface 42 of the concave portion 4. Accordingly, the generation of the concave meniscus is prevented. Furthermore, when the generation of the concave meniscus is prevented, the liquid surface is flattened and the thickness of the portion of the culture solution S in the vicinity of the inner circumferential surface 42 of the concave portion 4 is not larger than the thickness of other portions of the culture solution S. Therefore, the cell seeding amount per a unit area of the bottom surface 41 of the concave portion 4 does not increase near the inner circumferential surface 42 of the concave portion 4. This makes it possible to uniformly seed the cells.

Subsequently, the lid 2 is attached to the culture container body 1A to seal the opening 43 of the concave portion 4 (lid attaching step). When the culture container body 1A is used alone, the lid attaching step is omitted.

Subsequently, the cells are cultured inside the concave portion 4 according to a conventional method (cell culturing step). In the cell culturing step, components such as amino acids and proteins contained in the culture solution are hardly adsorbed onto the water repellent layer 5 formed on the inner circumferential surface 42 of the concave portion 4. It is therefore possible to prevent the generation of a concave meniscus due to the adsorption of components in the culture solution onto the water repellent layer 5 formed on the inner circumferential surface 42 of the concave portion 4 and the hydrophilization of the surface of the water repellent layer 5. In other words, throughout the cell culturing step, it is possible to maintain a state in which a concave meniscus is not generated.

In the case where the cells cultured in the concave portion 4 are adhering cells, the cell culturing method using the culture container 10A may include a step (extracellular matrix layer forming step) of, before the cell seeding step, forming an extracellular matrix layer in a portion or the entirety of the central region 412 of the bottom surface 41 of the concave portion 4.

The extracellular matrix layer contains extracellular matrix components (e.g., proteins, etc.). The extracellular matrix is a material that serves as a scaffold of cells when the cells are cultured.

In the extracellular matrix layer forming step, for example, an extracellular matrix solution is added to the central region 412 of the bottom surface 41 of the concave portion 4, and an extracellular matrix is adsorbed onto a portion or the entirety of the central region 412, whereby an extracellular matrix layer is formed.

The addition of the extracellular matrix solution to the central region 412 may be added in a small amount (e.g., drop-wise) such that the added extracellular matrix solution gradually spreads toward the peripheral edge of the bottom surface 41.

The extracellular matrix solution may be prepared by, for example, diluting a commercially available extracellular matrix at an appropriate concentration in a suitable solvent (e.g., phosphate buffered saline). For example, by leaving the extracellular matrix solution added to the central region 412 for 2 hours or more in an environment of 37 degrees C. or for one night or more in an environment of 4 degrees C., it is possible to cause the extracellular matrix to be adsorbed onto a portion or the entirety of the central region 412. After leaving the extracellular matrix solution, the remaining extracellular matrix solution is removed.

As shown in FIG. 6, the extracellular matrix solution M added to the central region 412 spreads toward the peripheral edge of the bottom surface 41. When reaching the outer edge region 411, the extracellular matrix solution M is repelled by the water repellent layer 5 formed in the outer edge region 411. Thus, the extracellular matrix solution M becomes a droplet and remains in the central region 412. Therefore, it is possible to efficiently adsorb the extracellular matrix onto a portion or the entirety of the central region 412. This gives rise to the following two major effects. One effect is that the extracellular matrix solution M can be selectively introduced into only the central region 412 in which cell culture is performed, thereby reducing the loss of the extracellular matrix which is generally expensive. The other effect is that the adsorption of the extracellular matrix onto the water repellent layer 5 formed on the inner circumferential surface 42 of the concave portion 4 is suppressed, thereby making it possible to prevent the generation of a concave meniscus due to the adsorption of the extracellular matrix onto the water repellent layer 5 formed on the inner circumferential surface 42 of the concave portion 4 and the hydrophilization of the surface of the water repellent layer 5.

Hereinafter, a cell observation method using the culture container 10A will be described. In the present embodiment, the culture container body 1A is used in combination with the lid 2. However, the culture container body 1A may be used alone.

The cell observation method using the culture container 10A includes a step of observing the cells in the concave portion 4 with a microscope from the side of the bottom surface 41 or the side of the opening 43 of the concave portion 4.

Examples of the microscope used for observation include an optical microscope such as a phase difference microscope or the like. Examples of the microscope to be used when observing the cells in the concave portion 4 from the side of the bottom surface 41 of the concave portion 4 includes an inverted microscope (an incident-light-type inverted microscope or a transmission-type inverted microscope), and the like. Examples of the microscope to be used when observing the cells in the concave portion 4 from the side of the opening 43 of the concave portion 4 include an upright microscope (an incident-light-type upright microscope or a transmission-type upright microscope), and the like.

In the case of using the incident-light-type inverted microscope, for example, light is irradiated from a light source installed under the culture container 10A toward the inside of the concave portion 4 through the bottom wall portion 31 of the culture container body 1A, and the light reflected by the cells in the concave portion 4 is received by the incident-light-type inverted microscope installed under the culture container 10A through the bottom wall portion 31 of the culture container body 1A, whereby the cells in the concave portion 4 can be observed.

In the case of using the transmission-type inverted microscope, for example, light is irradiated from a light source installed above the culture container 10A into the concave portion 4 through the lid 2, and the light transmitted through the concave portion 4 is received by the transmission-type inverted microscope installed under the culture container 10A through the bottom wall portion 31 of the culture container body 1A, whereby the cells in the concave portion 4 can be observed.

In the case of using the incident-light-type upright microscope, light is irradiated from a light source installed above the culture container 10A into the concave portion 4 through the lid 2, and the light reflected by the cells in the concave portion 4 is received by the incident-light-type upright microscope installed above the culture container 10A through the lid 2, whereby the cells in the concave portion 4 can be observed.

In the case of using the transmission-type upright microscope, light is irradiated from a light source installed under the culture container 10A toward the inside of the concave portion 4 through the bottom wall portion 31 of the culture container body 1A, and the light transmitted through the concave portion 4 is received by the transmission-type upright microscope installed above the culture container 10A through the lid 2, whereby the cells in the concave portion 4 can be observed.

Figure 8:
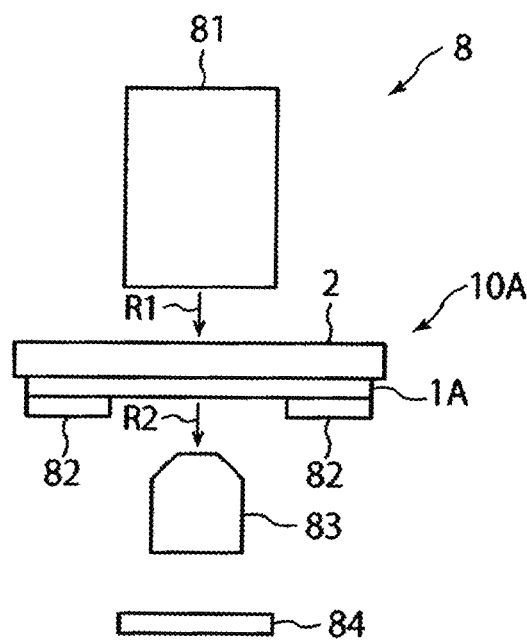
FIG. 8 is a schematic diagram of a transmission-type inverted microscope used for cell observation.

One embodiment in the case of using the transmission-type inverted microscope will be described below. In the present embodiment, the culture container body 1A is used in combination with the lid 2. However, the culture container body 1A may be used alone. As shown in FIG. 8, the transmission-type inverted microscope 8 is a phase difference microscope capable of capturing a phase difference image of cells. The transmission-type inverted microscope 8 includes an illumination optical system 81, a stage 82, an observation optical system 83 and an imaging element 84.

On the stage 82, the culture container 10A after cell culture is placed in a state in which the lid 2 is attached to the culture container body 1A. The cultured cells and the culture solution used for culture are accommodated in the concave portion 4 of the culture container 10A after cell culture. The cells in the concave portion 4 are objects to be observed.

The illumination optical system 81 generates illumination light suitable for generating a phase difference image and irradiates the same toward the culture container 10A held on the stage 82. The illumination optical system 81 may be configured similarly to the illumination optical system generally used for an optical microscope. For example, the illumination optical system 81 allows the light generated from a light source such as a halogen lamp or the like to pass through a field lens, a ring diaphragm, a condenser lens or the like, thereby adjusting the light into uniform illumination light suitable for generating a phase difference image. The illumination light is irradiated toward the culture container 10A on the stage 82.

The stage 82 supports the culture container 10A and adjusts the position of the culture container 10A. The stage 82 may be movable by a motor or the like in the vertical direction (the direction extending along an optical axis) and in the horizontal direction (the direction perpendicular to an optical axis).

The observation optical system 83 includes, for example, an objective lens, a phase difference plate, an imaging lens, and the like. The observation optical system 83 receives the light irradiated from the illumination optical system 81 and transmitted through the concave portion 4, and focuses a phase difference image.

The imaging element 84 captures the phase difference image of an observation target focused by the observation optical system 83. The imaging element 84 includes, for example, a CCD (Charge Coupled Device) image sensor, a CMOS (Complementary Metal Oxide Semiconductor) image sensor, and the like.

The operations of the illumination optical system 81, the stage 82, the observation optical system 83 and the imaging element 84 are controlled by a control part (not shown).

In the transmission-type inverted microscope 8, for example, instead of the imaging element 84, there may be provided an eyepiece or the like for allowing a human to observe an observation target with the naked eye.

Observation using the transmission-type inverted microscope 8 is performed as follows. The illumination light R1 is irradiated from the illumination optical system 81 to the culture container 10A held on the stage 82. The illumination light R1 enters the concave portion 4 through the lid 2 and passes through the concave portion 4. The transmitted light R2 transmitted through the bottom wall portion 31 of the culture container body 1A is received by the observation optical system 83, whereby a phase difference image is focused. The phase difference image of an observation target focused by the observation optical system 83 is captured by the imaging element 84. In this manner, the cells in the concave portion 4 are observed using the transmission-type inverted microscope 8.

When the water repellent layer 5 is not formed on the inner circumferential surface 42 of the concave portion 4, the inner circumferential surface 42 of the concave portion 4 having hydrophilicity is exposed to the internal space of the concave portion 4. Therefore, as shown in FIG. 7A, when the culture solution S is accommodated in the concave portion 4, the culture solution S is strongly attracted to the inner circumferential surface 42. As a result, the thickness of the portion S1 of the culture solution S in the vicinity of the inner circumferential surface 42 becomes larger than the thickness of other portions of the culture solution S. Thus, there is generated a phenomenon that the liquid surface of the culture solution S is bent concavely, namely a concave meniscus. When the concave meniscus is generated, the optical axis is distorted due to the inclination of the liquid surface in the vicinity of the inner circumferential surface 42. Therefore, it is difficult or impossible to observe the cells existing in the portion S1 near the inner circumferential surface 42. In contrast, as shown in FIG. 7B, the water repellent layer 5 is formed on the bottom surface 41 and the inner circumferential surface 42 of the concave portion 4 in the culture container body 1A according to the present embodiment. Therefore, the culture solution S in the vicinity of the inner circumferential surface 42 of the concave portion is not strongly attracted to the inner circumferential surface 42 of the concave portion 4. Accordingly, the generation of a concave meniscus is prevented. For this reason, the distortion of the optical axis due to the inclination of the liquid surface does not occur in the vicinity of the inner circumferential surface 42. Thus, the cells existing in the vicinity of the inner circumferential surface 42 can be observed. That is to say, the field of view for microscope observation is enlarged.

As shown in FIG. 7B, the outer edge region 411 of the bottom surface 41 of the concave portion 4 is a region where the cells are difficult to adhere due to the formation of the water repellent layer 5. Therefore, when the cells cultured in the culture container 10A are adhering cells, no or few cells is present in this region. Even if the generation of the concave meniscus is prevented, when the width W1 of the outer edge region 411 is larger than or equal to the width W2, the effect of enlarging the microscope observation field of view obtained by the concave meniscus prevention is lost. Therefore, the width W1 of the outer edge region 411 may be smaller than the width W2. As in the present embodiment, when the radius of the concave portion 4 is sufficiently larger than the width W2 (for example, when the radius of the concave portion 4 is 17.5 mm or more), the width W2 is as large as about 10 mm. In this case, the width W1 of the outer edge region 411 may be 10 mm or less, specifically 5 mm or less. The lower limit value of the width W1 of the outer edge region 411 is not particularly limited, but may be 0.5 mm, specifically 1 mm.

Second Embodiment

A culture container 10B according to a second embodiment is a culture container for microscope observation, namely a culture container capable of culturing cells and capable of microscope-observing of cultured cells. Therefore, the culture container 10B is configured to satisfy the conditions required for the container for cell culture and the conditions required for the container for microscope observation. However, the configuration of the culture container 10B may be appropriately changed as long as the culture container 10B can culture cells. When the culture container is not for microscope observation, it is not necessary to satisfy the conditions required for the container for microscope observation.

Figure 9:
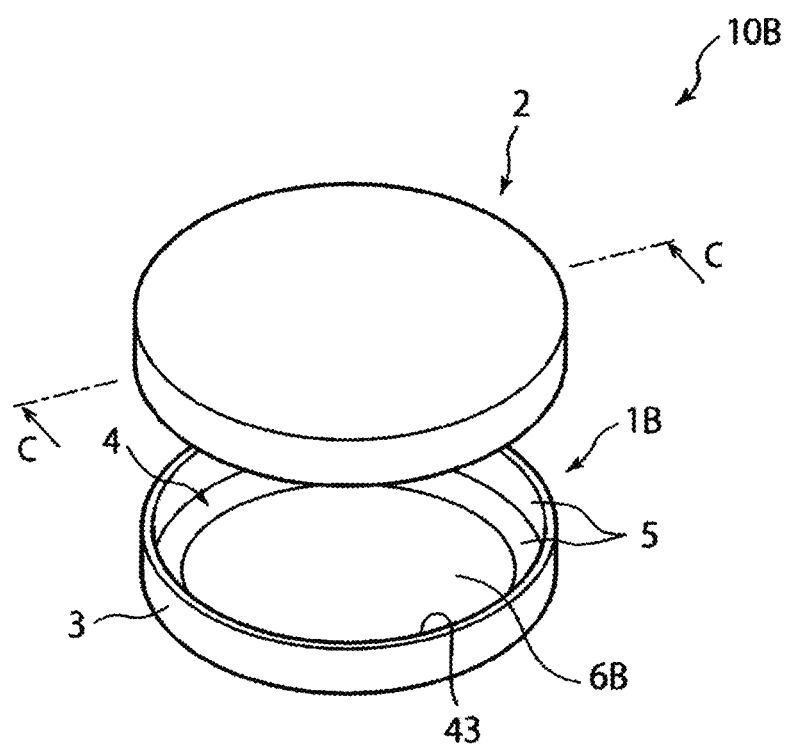
FIG. 9 is a perspective view of a culture container according to a second embodiment.
Figure 10:
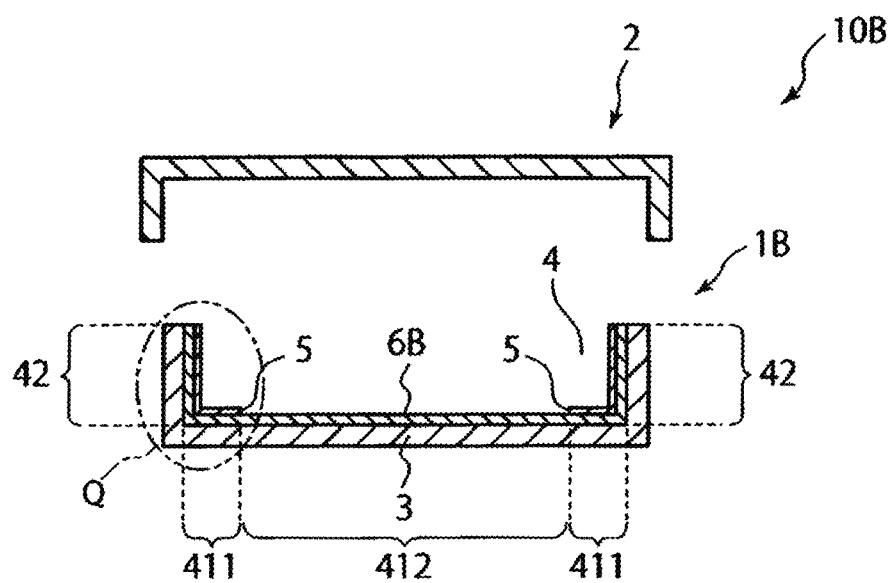
FIG. 10 is a sectional view of the culture container taken along line C-C in FIG. 9.

As shown in FIGS. 9 and 10, the culture container 10B includes a culture container body 1B and a lid 2. In the following description, the difference between the culture container 10B and the culture container 10A will be mainly described. The description on the culture container 10A will be applied to other points.

The culture container body 1B differs from the culture container body 1A according to the first embodiment in that a water repellent layer 5 is formed on the outer edge region 411 of the bottom surface 41 of the concave portion 4 and the inner circumferential surface 42 of the concave portion 4 via an intermediate layer 6B. In other points, the culture container body 1B is the same as the culture container body 1A. In the culture container body 1B according to the second embodiment, the same members or parts as those of the culture container body 1A are denoted by the same reference numerals.

As shown in FIGS. 9 and 10, the intermediate layer 6B formed on the entire bottom surface 41 of the concave portion 4 and the entire inner circumferential surface 42 of the concave portion 4 differs from the intermediate layer 6A formed on the entire outer edge region 411 of the bottom surface 41 and the entire inner circumferential surface 42 of the concave portion 4 but not formed in the central region 412 of the bottom surface 41.

As shown in FIGS. 9 and 10, the intermediate layer 6B is formed on the entire bottom surface 41 of the concave portion 4 and the entire inner circumferential surface 42 of the concave portion 4. The intermediate layer 6B includes a first portion extending over the entire outer edge region 411 of the bottom surface 41, a second portion extending over the entire inner circumferential surface 42, and a third portion extending over the entire central region 412 of the bottom surface 41. An edge portion of the first portion of the intermediate layer 6B at the side of the inner circumferential surface 42 is continuous with an edge portion of the second portion of the intermediate layer 6B at the side of the bottom surface 41. An edge portion of the first portion of the intermediate layer 6B at the side of the central region 412 is continuous with an edge portion of the third portion of the intermediate layer 6B.

As shown in FIGS. 9 and 10, one surface of the intermediate layer 6B includes a first region corresponding to the surface of the first portion of the intermediate layer 6B, a second region corresponding to the surface of the second portion of the intermediate layer 6B, and a third region corresponding to the surface of the third portion of the intermediate layer 6B. The first portion of the water repellent layer 5 is formed in the first region of one surface of the intermediate layer 6B, and the second portion of the water repellent layer 5 is formed in the second region of one surface of the intermediate layer 6B. An edge portion of the first portion of the water repellent layer 5 at the side of the boundary line L1 coincides with the boundary line L1 in a plan view.

Figure 11:
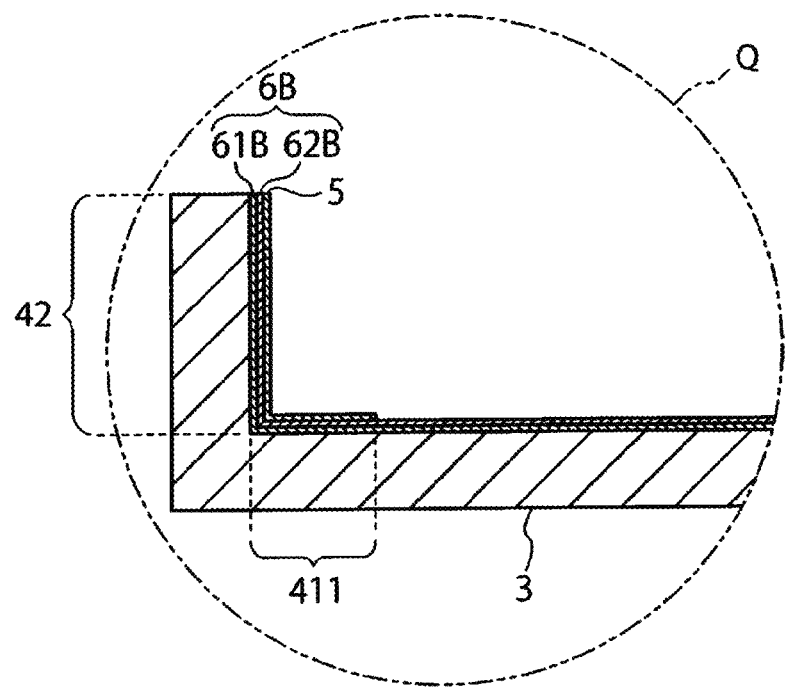
FIG. 11 is an enlarged view of a portion indicated by reference symbol Q in FIG. 10.

As shown in FIG. 11, the intermediate layer 6B includes a DLC layer 61B formed on the other surface side of the water repellent layer 5 and an adhesion layer 62B formed between the water repellent layer 5 and the DLC layer 61B. The DLC layer 61B and the adhesion layer 62B are configured similarly to the DLC layer 61A and the adhesion layer 62A.

As the water repellent layer 5 is formed on the entire outer edge region 411 of the bottom surface 41 of the concave portion 4 and the entire inner circumferential surface 42 of the concave portion 4 via the intermediate layer 6B, a culture chamber is formed inside the concave portion 4. One surface of the water repellent layer 5 is exposed to the internal space of the concave portion 4. A region corresponding to the surface of the first portion of the water repellent layer 5 in one surface of the water repellent layer 5 forms an outer edge region of a bottom surface of the culture chamber. A region corresponding to the surface of the second portion of the water repellent layer 5 in one surface of the water repellent layer 5 forms an inner circumferential surface of the culture chamber. As a result, water repellency is imparted to the outer edge region of the bottom surface of the culture chamber and the inner circumferential surface of the culture chamber. A region corresponding to the surface of the third portion of the intermediate layer 6B in one surface of intermediate layer 6B is exposed to the internal space of the concave portion 4 and forms a central region of the bottom surface of the culture chamber. As a result, hydrophilicity is imparted to the central region of the bottom surface of the culture chamber.

The culture container body 1B may be manufactured by a method including:

(B1) a step of preparing a base 3 having a concave portion 4 formed therein;

(B2) a step of forming the DLC layer 61B on the entire bottom surface 41 and the entire inner circumferential surface 42 of the concave portion 4;

(B3) a step of forming the adhesion layer 62B on the entire one surface of the DLC layer 61B formed in step (B2); and (B4) a step of forming the water repellent layer 5 in a region corresponding to the outer edge region 411 of the bottom surface 41 and a region corresponding to the inner circumferential surface 42 in one surface of the adhesion layer 63B formed in step (B3).

Steps (B1) to (B4) may be performed in the same manner as the manufacturing process of the culture container body 1A.

In step (B4), a region other than the region forming the water repellent layer 5 in one surface of the adhesion layer 62B may be covered with a masking material.

The culture container 10B may be used for a cell culture method and a cell observation method in the same manner as the culture container 10A.

Third Embodiment

A culture container 10C according to a third embodiment is a culture container for microscope observation, namely a culture container capable of culturing cells and capable of microscope-observing cultured cells. Therefore, the culture container 10C is configured to satisfy the conditions required for the container for cell culture and the conditions required for the container for microscope observation. However, the configuration of the culture container 10C may be appropriately changed as long as the culture container 10C can culture cells. When the culture container is not for microscope observation, it is not necessary to satisfy the conditions required for the container for microscope observation.

Figure 12:
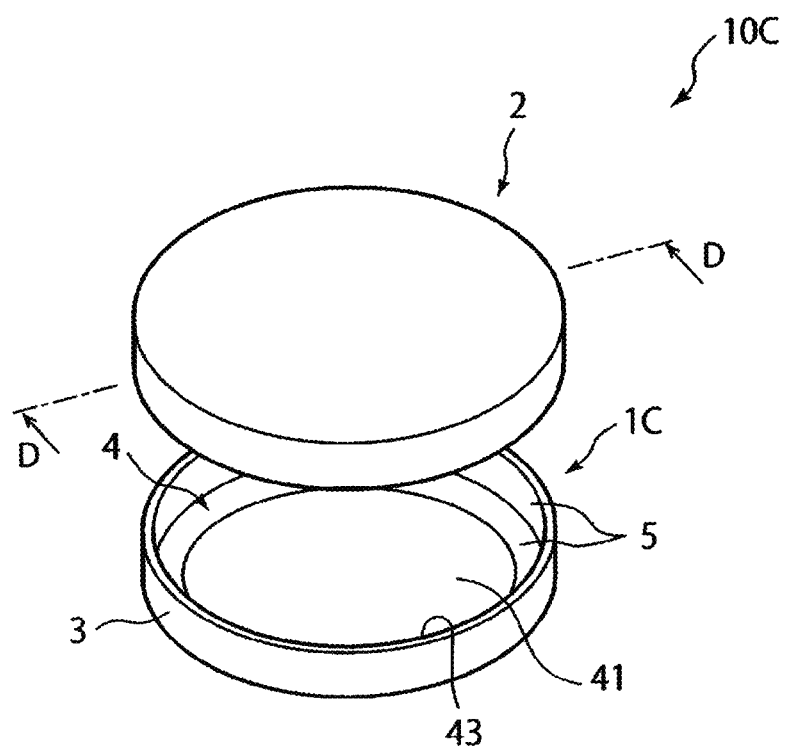
FIG. 12 is a perspective view of a culture container according to a third embodiment.
Figure 13:
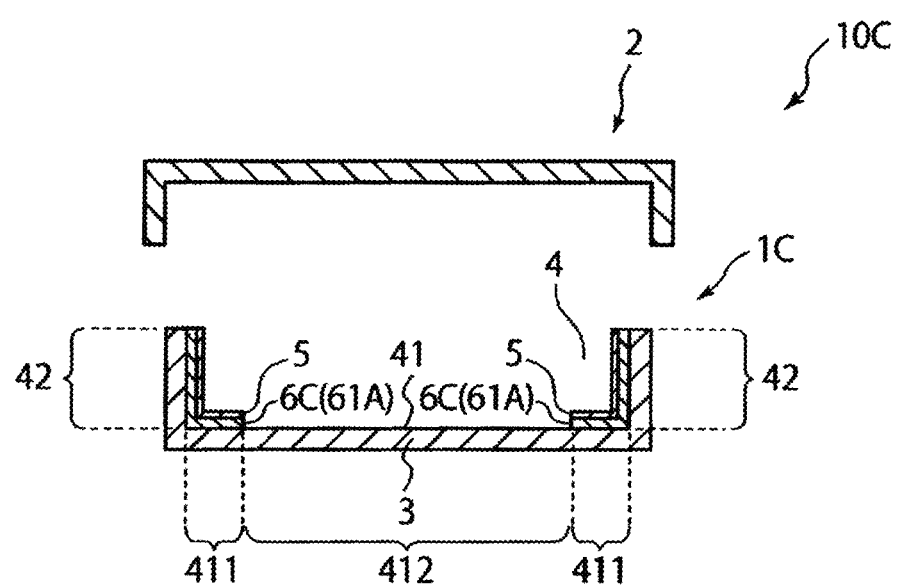
FIG. 13 is a sectional view of the culture container taken along line D-D in FIG. 12.

As shown in FIGS. 12 and 13, the culture container 10C includes a culture container body 1C and a lid 2. In the following description, the difference between the culture container 10C and the culture container 10A will be mainly described. The description on the culture container 10A will be applied to other points.

The culture container body 1C differs from the culture container body 1A according to the first embodiment in that a water repellent layer 5 is formed on the entire outer edge region 411 of the bottom surface 41 of the concave portion 4 and the entire inner circumferential surface 42 of the concave portion 4 via an intermediate layer 6C. Other points are the same as those of the culture container body 1A. In the culture container body 1C according to the third embodiment, the same members or parts as those of the culture container body 1A are denoted by the same reference numerals.

As shown in FIGS. 12 and 13, the intermediate layer 6C including a DLC layer 61A differs from the intermediate layer 6A including the DLC layer 61A and the adhesion layer 62A in that the intermediate layer 6C does not include the adhesion layer 62A. Other configurations of the intermediate layer 6C are the same as those of the intermediate layer 6A.

The water repellent layer 5 is formed on the entire outer edge region 411 of the bottom surface 41 of the concave portion 4 and the entire inner circumferential surface 42 of the concave portion 4 via the intermediate layer 6C, whereby a culture chamber is formed inside the concave portion 4. One surface of the water repellent layer 5 is exposed to the internal space of the concave portion 4. The region corresponding to the surface of the first portion of the water repellent layer 5 in one surface of the water repellent layer 5 forms an outer edge region of a bottom surface of the culture chamber. The region corresponding to the surface of the second portion of the water repellent layer 5 in one surface of the water repellent layer 5 forms an inner circumferential surface of the culture chamber. As a result, water repellency is imparted to the outer edge region of the bottom surface and the inner circumferential surface of the culture chamber. In the bottom surface 41 of the concave portion 4, a region where the water repellent layer 5 is not formed, namely the central region 412, is exposed to the internal space of the concave portion 4 and forms a central region of the bottom surface of the culture chamber. As a result, hydrophilicity is imparted to the central region of the bottom surface of the culture chamber.

The culture container body 1C may be manufactured by a method including:

(C1) a step of preparing a base 3 having a concave portion 4 formed therein;

(C2) a step of masking the central region 412 of the bottom surface 41 of the concave portion 4;

(C3) a step of forming the DLC layer 61A on the entire outer edge region 411 of the bottom surface 41 of the concave portion 4 and the entire inner circumferential surface 42 of the concave portion 4; and (C4) a step of forming the water repellent layer 5 on the entire one surface of the DLC layer 61A formed in step (C3).

Steps (C1) to (C4) may be performed in the same manner as the manufacturing process of the culture container body 1A.

The culture container 10C may be used for a cell culture method and a cell observation method in the same manner as the culture container 10A.

EXAMPLES

Example 1

A commercially available polystyrene-made φ35 mm culture dish (FALCON Inc., model number 353001) was prepared. This culture dish includes a circular bottom wall portion and a peripheral wall portion standing up from the peripheral edge of the bottom wall portion to form a concave portion. The culture dish is integrally molded by a polystyrene material. The surface of the concave portion includes a bottom surface formed by the bottom wall portion and an inner circumferential surface standing up from the peripheral edge of the bottom surface. The entire surface of the concave portion is subjected to a hydrophilization treatment.

Regions other than the outer edge region in the bottom surface of the concave portion were covered with a commercially available masking material. The outer edge region was set as an annular region having an outer peripheral line coinciding with an outer peripheral line of the bottom surface of the concave portion and an inner peripheral line having a distance of 5 mm from the outer peripheral line of the bottom surface of the concave portion.

A diamond-like carbon (DLC) coating layer was formed on the entire outer edge region of the bottom surface of the concave portion and the entire inner circumferential surface of the concave portion. The DLC layer was formed with a thickness of 0.5 μm by a plasma CVD method. As a film forming gas, a mixed gas of $C_2H_2$ and $C_6H_5CH_3$ was used.

After forming the DLC layer, a $SiO_2$ layer was formed as an adhesion layer on the DLC layer. The $SiO_2$ layer was formed with a film thickness of 1.0 μm by coating TEOS (manufactured by High Purity Science Co., Ltd.) on the DLC layer by a spraying method and then drying and curing the TEOS.

After forming the adhesion layer, a water repellent layer was formed on the adhesion layer. The water repellent layer was formed with a thickness of 0.1 μm by coating a compound containing fluorinated polysiloxane on the DLC layer by a spraying method and then drying and curing the compound.

After forming the water repellent layer, the masking material was removed. The contact angle with the pure water on the surface of the water repellent layer was measured by a θ/2 method (PG-X manufactured by Matsubo Corporation). The contact angle was 110 to 120 degrees (central value 115 degrees). Thereafter, ReproFF2 (ReproCell Inc., model number RCHEMD006A), which is a culture solution for iPS cell culture, was introduced into the concave portion. Thereafter, the interior of the concave portion into which the culture solution is introduced was observed using an inverted phase difference microscope (Olympus Corporation, model number IX-81) according to a conventional method. The microscope observation was carried out under the condition that the culture solution is allowed to stand at 37 degrees C. in a 5% $CO_2$ incubator for 8 days, similarly to ordinary cell culture conditions.

Figure 14:
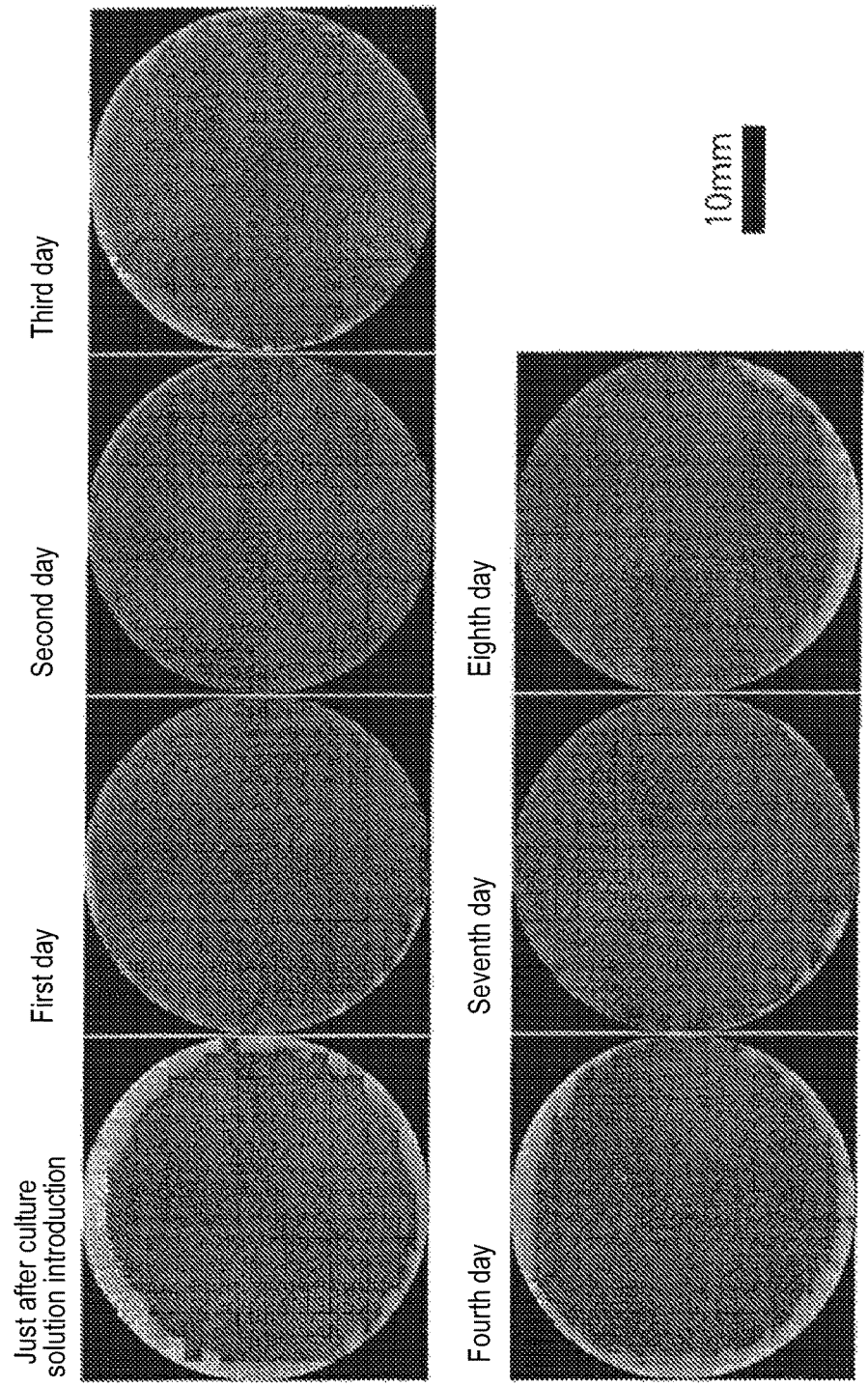
FIG. 14 is a view showing a microscope observation image of a culture dish on which a water repellent layer is formed.

The microscope observation results are shown in FIG. 14. As shown in FIG. 14, the proportion of the observable area in the microscopic field of view was 84% immediately after introduction of the culture solution, 99% on the first day of culture, 100% on the second day of culture, 96% on the third day of culture, 89% on the fourth day of culture, 99% on the seventh day of culture, and 95% on the eighth day of culture. When averaging the proportions of the observable area until the eighth day, 95% of the total area was observable with the phase difference microscope, and only 5% of the total area was not observable with the phase difference microscope.

From these results, it was shown that the generation of a concave meniscus can be suppressed and clear observation can be realized over a wide range by forming the water repellent layer on the inner circumferential surface and the outer edge region of the bottom surface of the concave portion. It was also shown that the concave meniscus suppression effect was lasted for 8 days or more.

Example 2

A commercially available polystyrene-made φ35 mm culture dish (FALCON Inc., model number 353001) was prepared. Regions other than the outer edge region in the bottom surface of the concave portion were covered with a commercially available masking material. The outer edge region was set as an annular region having an outer peripheral line coinciding with an outer peripheral line of the bottom surface of the concave portion and an inner peripheral line having a distance of 5 mm from the outer peripheral line of the bottom surface of the concave portion.

As in Example 1, a DLC layer as a barrier layer, a $SiO_2$ layer as an adhesion layer, and a water repellent layer were formed.

After forming the water repellent layer, the masking material was removed. The contact angle with the pure water on the surface of the water repellent layer was measured by a θ/2 method (PG-X manufactured by Matsubo Corporation). The contact angle was 110 to 120 degrees (central value 115 degrees). Thereafter, Vitronectin-N (Life Technologies Inc., model number A14700) was coated as a protein serving as a scaffold of adhering cells on a region other than the outer edge region in the bottom surface of the concave portion (a region where no water repellent layer is formed) according to ordinary conditions.

Thereafter, iPS cells were cultured using ReproFF2 (ReproCell Inc., model number RCHEMD006A) which is a culture solution for culturing iPS cells. The cell culture was carried out under the condition that the iPS cells are allowed to stand at 37 degrees C. in a 5% $CO_2$ incubator for 10 days, similarly to ordinary cell culture conditions.

The interior of the concave portion was observed over time according to a conventional method using an inverted phase difference microscope (Olympus Corporation, model number IX-81) and was compared with that of an ordinary culture dish on which a water repellent layer is not formed.

Figure 15:
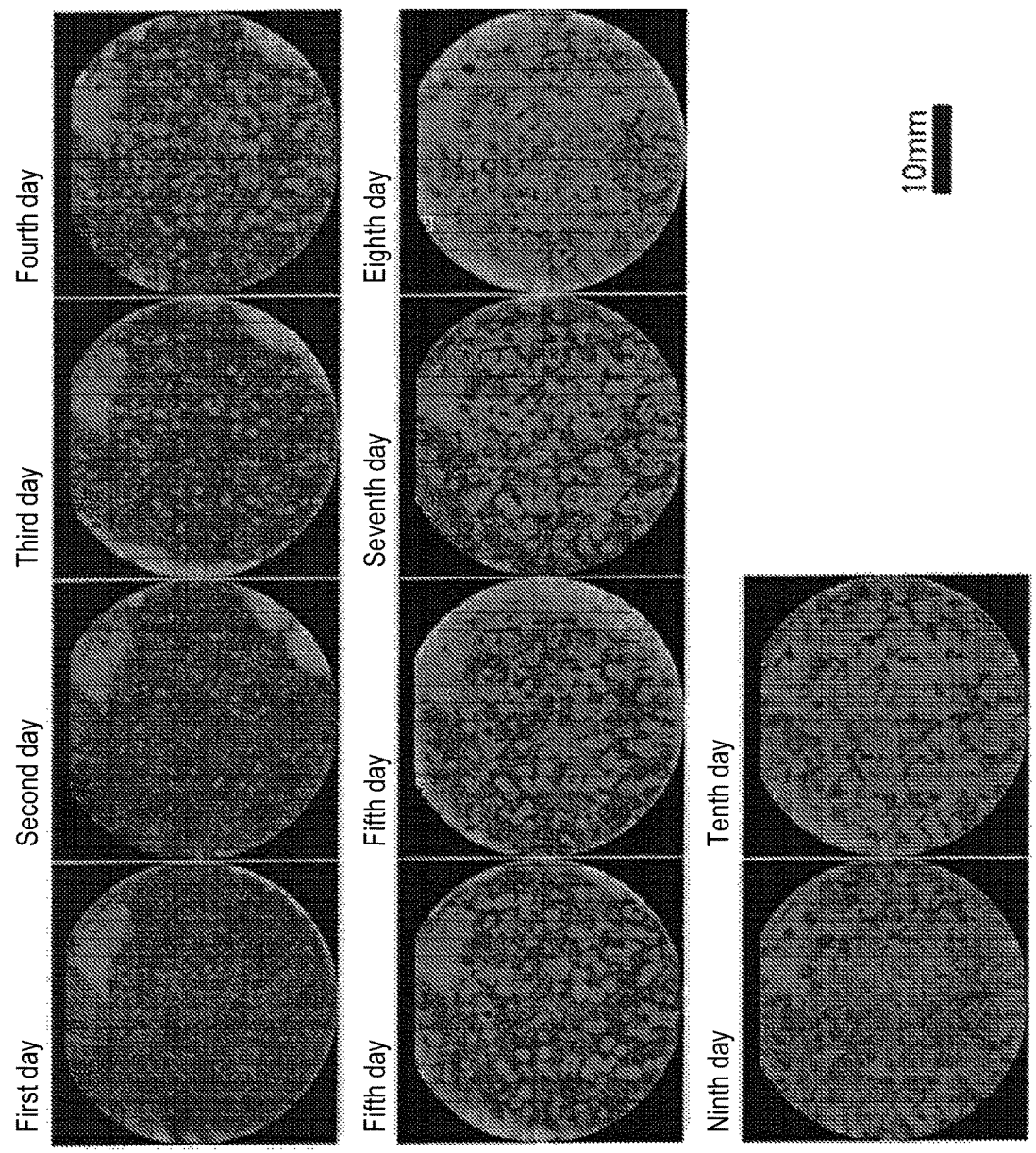
FIG. 15 is a view showing a microscope observation image of a culture dish on which a water repellent layer is formed.
Figure 16:
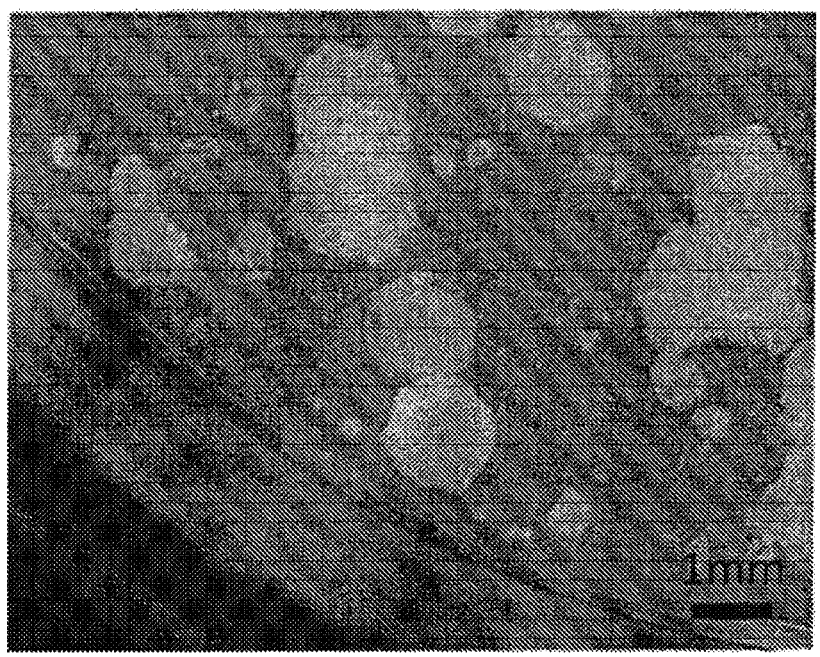
FIG. 16 is a view showing a microscope observation image of a culture dish on which a water repellent layer is formed.
Figure 17:
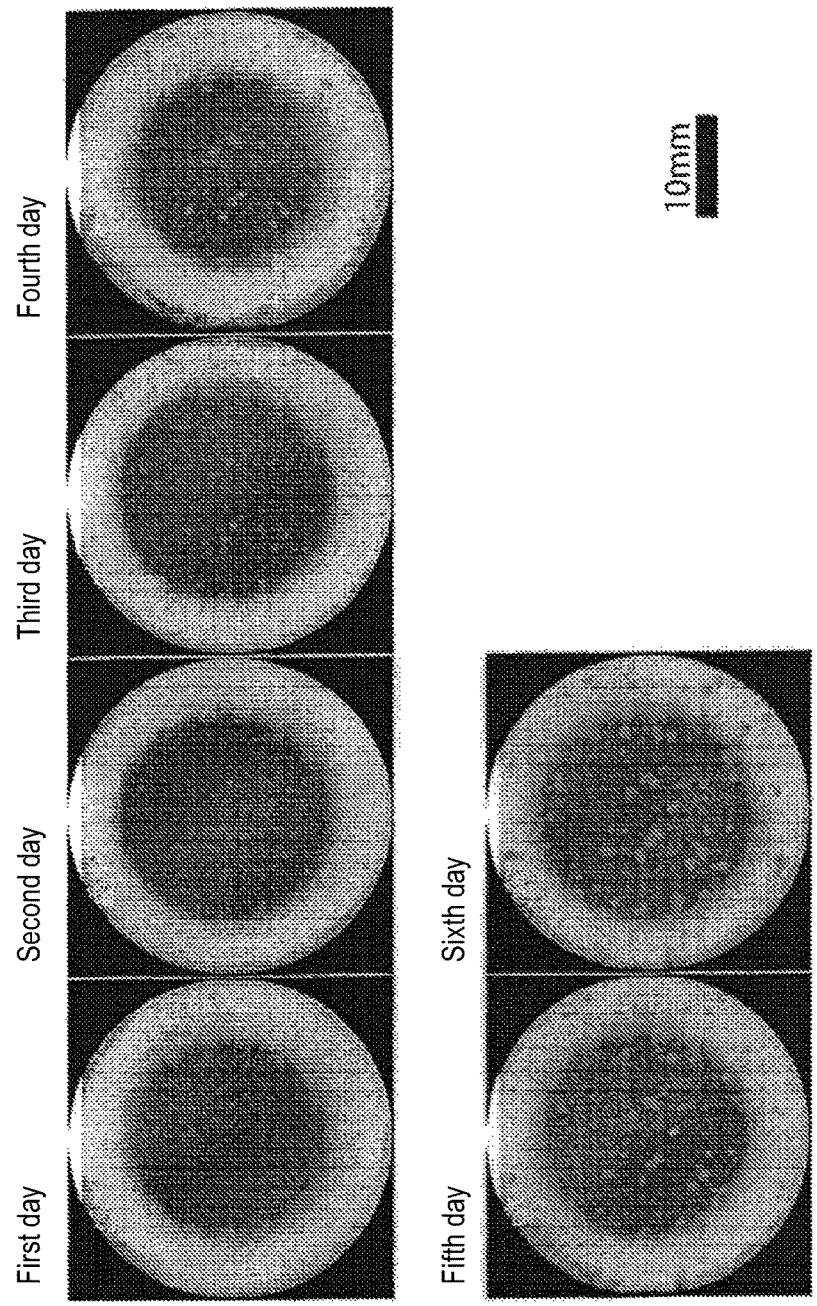
FIG. 17 is a view showing a microscope observation image of an ordinary culture dish on which a water repellent layer is not formed.

The microscope observation results are shown in FIGS. 15 to 17. FIGS. 15 and 16 show microscope observation images of a culture dish with a water repellent layer formed thereon and, FIG. 17 shows a microscope observation image of an ordinary culture dish with no water repellent layer formed thereon.

As shown in FIG. 15, in the culture dish with the water repellent layer formed thereon, the proportion of the observable area in the microscopic field of view was 98% on the first day of culture, 96% on the second day of culture, 93% on the third day of culture, 97% on the fourth day of culture, 96% on the fifth day of culture, 87% on the sixth day of culture, 98% on the seventh day of culture, 87% on the eighth day of culture, 98% on the ninth day of culture, and 94% on the tenth day of culture. When averaging the proportions of the observable area until the tenth day, 94% of the total area was observable with the phase difference microscope, and only 6% of the total area was not observable with the phase difference microscope. As shown in FIG. 16, the cells cultured in the vicinity of the inner circumferential surface of the concave portion could also be observed with the phase difference microscope. Furthermore, it was confirmed that the iPS cells have no problem and could be cultured as usual. In the outer edge region of the bottom surface of the concave portion, namely in the portion not coated with a protein serving as a scaffold of adhering cells, the cells were observed in a state in which they are floating in the culture solution contained in the culture dish.

On the other hand, as shown in FIG. 17, in the ordinary culture dish with no water repellent layer formed thereon, the proportion of the observable area in the microscopic field of view was 37% on the first day of culture, 43% on the second day of culture, 44% on the third day of culture, 34% on the fourth day of culture, 41% on the fifth day of culture, and 45% on the sixth day of the culture. When averaging the proportions of the observable area until the sixth day, only 41% of the total area was observable with the phase difference microscope, and the remaining 59% of the total area was not observable with the phase difference microscope.

From these results, it was shown that the generation of a concave meniscus can be suppressed and clear observation can be realized over a wide range by forming the water repellent layer on the outer edge region of the bottom surface of the concave portion and the inner circumferential surface of the concave portion. It was also shown that the concave meniscus suppression effect was lasted for 10 days or more under the condition that the iPS cells are cultured.

Example 3

A commercially available polystyrene-made φ35 mm culture dish (FALCON Inc., model number 353001) was prepared. The entire inner circumferential surface of the concave portion was subjected to a water repellency treatment so that the contact angle with the pure water on the surface of the water repellent layer in the contact angle measurement using a θ/2 method (PG-X manufactured by Matsubo Corporation) becomes 60 degrees, 90 degrees, 100 to 110 degrees (central value 105 degrees) or 110 to 120 degrees (central value 115 degrees). Then, ReproFF2 (ReproCell Inc., model number RCHEMD006A), which is a culture solution for iPS cell culture, was introduced into the concave portion. Thereafter, the interior of the concave portion into which the culture solution is introduced was observed according to a conventional method using an inverted phase difference microscope (Olympus Corporation, model number IX-81).

Figure 18:
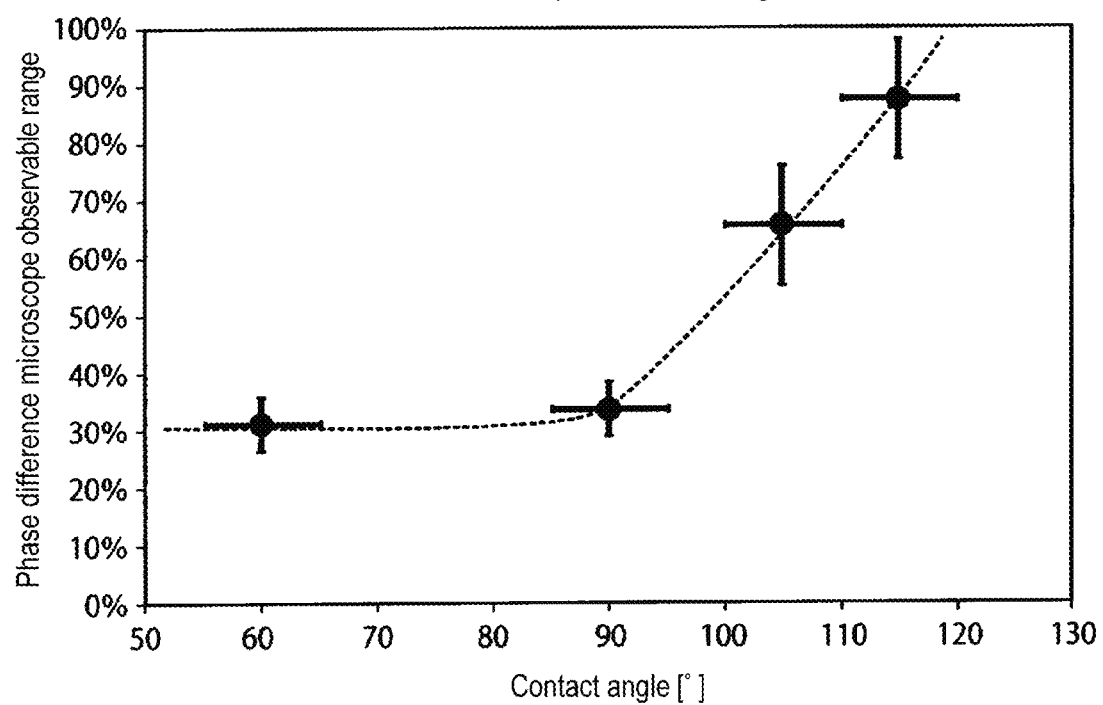
FIG. 18 is a view showing a relationship between a contact angle and a phase difference microscope observable range.

The results are shown in FIG. 18. FIG. 18 is a diagram showing the relationship between the contact angle and the observable range of the phase difference microscope. As shown in FIG. 18, the proportion of observable area in the microscopic field of view is 31% at a contact angle of 60 degrees, 34% at a contact angle of 90 degrees, 66% at a contact angle of 100 to 110 degrees (central value 105 degrees), and 88% at a contact angle of 110 to 120 degrees (central value 115 degrees).

From these results, it was shown that the concave meniscus suppressing effect appears when the contact angle is 90 degrees or more, the concave meniscus suppressing effect is further improved when the contact angle is 105 degrees or more, and the concave meniscus suppressing effect is even further improved when the contact angle is 115 degrees or more. The function and effect of the water repellent layer shown in the above examples are not dependent on the type of the culture container, but are demonstrated not only in the culture dish (FALCON Inc., model number 353001) used in the examples but also in various commercially available culture containers including culture dishes in which the surface of a concave portion is not subjected to a hydrophilization treatment.

EXPLANATION OF REFERENCE NUMERALS 10A to 10C: culture container, 1A to 1C: culture container body, 2: lid, 3: base, 4: concave portion, 41: bottom surface of concave portion, 411: outer edge region of bottom surface of concave portion, 412: central region of bottom surface of concave portion, 42: inner circumferential surface of concave portion, 5: water repellent layer, 6A to 6C: intermediate layer, 61A and 61B: DLC layer, 62A and 62B: adhesion layer

The invention claimed is:

1. A culture container, comprising:
   a base having a concave portion formed therein;
   a water repellent layer formed only on an outer edge region of a bottom surface of the concave portion and an inner circumferential surface of the concave portion;
   and a central region having hydrophilicity and located inward of the outer edge region of the bottom surface of the concave portion,
   wherein the outer edge region is formed in an annular shape along an outer peripheral line of the bottom surface of the concave portion,
   wherein one surface of the water repellent layer is exposed to an internal space of the concave portion.

2. The culture container of claim 1, wherein the bottom surface of the concave portion is a flat surface.

3. The culture container of claim 1, wherein a contact angle between the one surface of the water repellent layer and water is 115 degrees or more.

4. A culture container, comprising:
   a base having a concave portion formed therein;
   a water repellent layer formed on an outer edge region of a bottom surface of the concave portion and an inner circumferential surface of the concave portion;
   a central region having hydrophilicity and located inward of the outer edge region of the bottom surface of the concave portion; and
   a DLC layer formed at a side of the other surface of the water repellent layer,
   wherein the outer edge region is formed in an annular shape along an outer peripheral line of the bottom surface of the concave portion,
   and wherein one surface of the water repellent layer is exposed to an internal space of the concave portion.

5. The culture container of claim 4, further comprising:
   an adhesion layer formed between the water repellent layer and the DLC layer.

6. A method of culturing cells using the culture container of claim 1, comprising:

forming an extracellular matrix layer in a region other than the outer edge region in the bottom surface of the concave portion, before seeding the cells in the concave portion.

7. A method of observing cells using the culture container of claim 1, comprising:
observing the cells in the concave portion with a phase difference microscope from a side of the bottom surface of the concave portion or a side of an opening of the concave portion.

* * * * *